United States Patent [19]

Sugawara et al.

[11] Patent Number: 4,751,299
[45] Date of Patent: Jun. 14, 1988

[54] OPTICALLY ACTIVE β-LACTAMS AND METHOD OF THEIR PRODUCTION

[75] Inventors: Tohru Sugawara, Toyono; Yasuhiko Kawano, Suita; Kouichi Yoshioka, Kyoto, all of Japan

[73] Assignee: Takeda Chemical Industries, Ltd., Osaka, Japan

[21] Appl. No.: 671,076

[22] Filed: Nov. 13, 1984

[30] Foreign Application Priority Data

Nov. 18, 1983 [JP] Japan ................................. 58-217990
Nov. 2, 1984 [JP] Japan ................................. 59-232162

[51] Int. Cl.$^4$ .................. C07D 205/08; C07D 403/04; C07D 403/12; C07D 403/14
[52] U.S. Cl. ..................................... 540/364; 540/363
[58] Field of Search ................. 260/239 A, 245.4; 540/363, 364

[56] References Cited

U.S. PATENT DOCUMENTS

| | | | |
|---|---|---|---|
| 4,068,072 | 1/1978 | Tsushima | 260/245.2 R |
| 4,138,553 | 2/1979 | Ishimoto | 544/18 |
| 4,181,800 | 1/1980 | Kamiya et al. | 544/180 |
| 4,427,689 | 1/1984 | Zomaya | 260/245.3 |
| 4,467,101 | 8/1984 | Kocsis | 560/33 |
| 4,473,502 | 9/1984 | Liu | 260/239 A |
| 4,476,124 | 10/1984 | Heymes | 514/210 |
| 4,526,962 | 7/1985 | Farge | 544/22 |
| 4,550,105 | 10/1985 | Matsuo | 260/239 A |
| 4,595,532 | 6/1986 | Miller | 544/359 |
| 4,595,539 | 6/1986 | Hamanaka | 260/239 AL |
| 4,595,677 | 6/1986 | Riniker | 514/17 |

OTHER PUBLICATIONS

Bose, "Spec. Pub—R. Soc. Chem., vol. 38, (1981)", pp. 80–87.
Tenneson, Chem. Abs., 93, 239341u, (1980).
Uyeo et al., Chem. Abs., 93, 220560t, (1980).
McOmie, "Protective Groups in Organic Chemistry", pp. 43–83.
Ojima et al., Tetrahedron Letters, vol. 22, pp. 3907–3910, (1980).
Just et al., Can. J. Chem., 56, 211–217, (1978).
Sharma et al., Chem. Abs., vol. 94, p. 736, No. 139522f.

Primary Examiner—Mark L. Berch
Attorney, Agent, or Firm—Wenderoth, Lind & Ponack

[57] ABSTRACT

Optically active β-lactams of the general formula

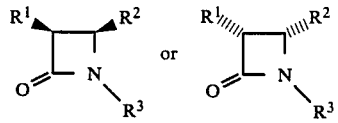

wherein $R^1$ is an amino or protected amino group, $R^2$ is an organic residue bonding through a carbon atom thereof and $R^3$ is the residue remaining after removal of the α-amino group from an optically active α-amino acid or a derivative thereof as well as a method of producing the same.

21 Claims, No Drawings

OPTICALLY ACTIVE β-LACTAMS AND METHOD OF THEIR PRODUCTION

This invention relates to optically active β-lactams and a method of producing the same. More specifically, it relates to optically active β-lactams of the general formula

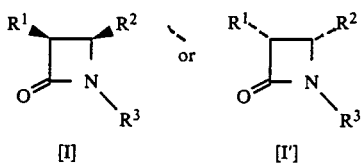

wherein $R^1$ is an amino or protected amino group, $R^2$ is an organic residue bonding through a carbon atom thereof and $R^3$ is the residue remaining after removal of the α-amino group from an optically active α-amino acid or a derivative thereof as well as a method of producing the same.

Methods of synthesizing optically active β-lactams starting from optically active α-amino acids have been known. Synthesis of 3-azido-4-substituted 2-azetidinone derivatives is reported in Canadial Journal of Chemistry, 56, 211–217 (1978), ibid., 58, 1605–1607 (1980), Tetrahedron Letters, 3907–3910 (1980) and The Journal of Organic Chemistry, 47, 4075–4081 (1982). In all cases, however, 2-azidoacetyl chloride, which is sometimes unstable or explosive and requires special care in handling, is used as a necessary reagent, so that the methods reported there can hardly be used on a commercial scale because of difficulties in process control. According to Tetrahedron Letters, 5119–5122 (1978), 2-phthalimidoacetyl chloride is used in place of 2-azidoacetyl chloride for synthesizing optically active β-lactams, which, however, have no substituent in position 4.

The present invention has overcome the drawbacks of the known methods and provides intermediates useful for the synthesis of a variety of β-lactam antibiotics and a method of producing such intermediates which can be used for industrial purposes.

As a result of the intensive research in an attempt to develop a novel and industrial method of producing optically active β-lactams, the present inventors have succeeded in preparing optically active β-lactams of general formula [I] and [I'] by utilizing optically active α-amino acids or derivatives thereof and have established a novel method of producing them at low costs and in a simple and industrially advantageous manner. These compounds are very useful, for example, as intermediates in the synthesis of a variety of antibiotics such as monocyclic β-lactams.

More specifically, the method of producing the compounds of general formula [I] or [I'] comprises reacting a substituted acetic acid of the general formula

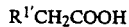 $R^{1'}CH_2COOH$ [II]

wherein $R^{1'}$ is a protected amino group, or a reactive derivative thereof resulting from modification of the carboxyl group, with a substituted methyleneamine compound of the general formula

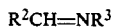 $R^2CH=NR^3$ [III]

wherein $R^2$ and $R^3$ are as defined above, and, if necessary, removing the protective group.

The substituent $R^{1'}$ in compound [II], which is one of the starting materials to be used in the practice of the invention, is a protected amino group, and the substituent $R^1$ in the objective compounds [I] and [I'] is an amino or protected amino group. As the amino-protecting group of the protected amino represented by $R^1$ or $R^{1'}$, there may be appropriately adapted those commonly used for the same purpose in the field of β-lactam and peptide synthesis, and there may be mentioned arylacyl, aliphatic acyl, arylsulfonyl, aliphatic sulfonyl groups, oxycarbonyl groups of the general formula $R°OCO—$, wherein $R°$ is as defined later herein, or other amino-protecting groups. These amino-protecting groups may be those which substitute for one hydrogen atom of the amino group and those which substitute for two hydrogen atoms thereof, and the latter includes a group which forms a nitrogen-containing ring structure together with the nitrogen atom of the amino group. The above-mentioned arylacyl, aliphatic acyl, arylsulfonyl or aliphatic sulfonyl groups may be substituted with $C_{1-6}$ alkyl (specific examples are as described later herein as an alkyl group of the substituent $R^2$), $C_{1-6}$ alkoxy (specific examples are as described later herein as an alkoxy group of the substituent $R^2$), substituted silyl group (e.g. trimethylsilyl, triethylsilyl, etc.), $C_{1-6}$ alkanoyl (specific examples are as described later herein as an acyl group), $C_{1-6}$ alkylsulfonyl (e.g. methanesulfonyl, ethanesulfonyl, etc.), nitro, cyano, halogen atom (e.g. fluorine, chlorine, etc.), and so on. The arylacyl group is preferably a $C_{7-12}$ arylacyl such as phthaloyl, benzoyl, 4-nitrobenzoyl or 4-tert-butylbenzoyl. The aliphatic acyl group is preferably of $C_{1-6}$ such as formyl, acetyl, propionyl, monochloroacetyl, dichloroacetyl, trichloroacetyl, trifluoroacetyl, maleoyl, or succinyl. The arylsulfonyl group is preferably of $C_{6-11}$ such as benzenesulfonyl, 4-tert-butylbenzenesulfonyl or para-toluenesulfonyl. The aliphatic sulfonyl group is preferably of $C_{1-6}$ and specific examples are as described above as examples of alkylsulfonyl group. As $R°$ of oxycarbonyl group of the general formula $R°OCO—$, there may be mentioned group such as $C_{1-6}$ alkyl, $C_{5-6}$ cycloalkyl, $C_{6-10}$ aryl or $C_{7-13}$ aralkyl, and these groups may be further substituted. Specific examples of such oxycarbonyl groups are methoxycarbonyl, ethoxycarbonyl, isopropoxycarbonyl, tert-butoxycarbonyl, 2-cyanoethoxycarbonyl, 2,2,2-trichloroethoxycarbonyl, 2-trimethylsilylethoxycarbonyl, benzyloxycarbonyl, 2-(methylsulfonyl)ethoxycarbonyl, 4-nitrobenzyloxycarbonyl, 4-methoxybenzyloxycarbonyl, diphenylmethyloxycarbonyl, methoxymethyloxycarbonyl, acetylmethyloxycarbonyl, isobornyloxycarbonyl, phenoxycarbonyl, etc. Specific examples of other amino-protecting groups are trityl, 2-nitrophenylthio, benzylidene, 4-nitrobenzylidene, benzyl, 4-nitrobenzyl, $R^4OCOCH=C(CH_3)—$, a group which forms protected amino group of the general formula

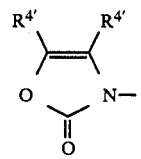

together with the amino group and substituted silyl groups such as $R^5R^6R^7Si-$, $di(R^5R^6R^7Si)-$ and $-Si(R^5R^6)XSi(R^7R^8)-$, wherein $R^4$, $R^5$, $R^6$, $R^7$ and $R^8$ each is a straight or branched $C_{1-6}$ alkyl (specific examples are as described later herein as an alkyl group of the substituent $R^2$) or an $C_{6-10}$ aryl group such as phenyl or naphthyl, $R^5$, $R^6$, $R^7$, $R^8$ may be the same or different, $R^{4'}$ is an aryl group such as phenyl or naphthyl and X is a lower alkylene group such as methylene or ethylene.

In the present invention, phthalimido or benzyloxycarbonylamino is most preferable as a protected amino group.

The organic residue $R^2$ bonding through a carbon atom thereof and existing in compound [III], another starting material, and in the objective compound [I] and [I'] includes, among others, alkyl, cycloalkyl, alkenyl, cycloalkenyl, alkynyl, aryl, aralkyl and heterocyclic groups, which may optionally have one to several substituents (preferably one to five). In the following, the upper right asterisk borne by a group name indicates that the group may have a substituent or substituents. Thus, for instance, "alkyl*" means "alkyl which may optionally have a substituent or substituents." The number of substituents is not limited to 1 but the group in question may have two to five substituents which are the same or different, as the case may be. The alkyl as $R^2$ is preferably a straight or branched $C_{1-6}$ alkyl such as methyl, ethyl, n-propyl, isopropyl, n-butyl, isobutyl, sec-butyl, tert-butyl, n-pentyl, isopentyl, tert-amyl, neopentyl, n-hexyl or isohexyl. The cycloalkyl is preferably a $C_{3-8}$ cycloalkyl, such as cyclopropyl, cyclobutyl, cyclopentyl, cyclohexyl, cycloheptyl or adamantyl. The alkenyl is preferably a straight or branched $C_{2-6}$ alkenyl such as vinyl, allyl, 1-propenyl, isopropenyl, 2-methallyl, crotyl, 1-butenyl, 2-butenyl or 3-butenyl. The alkynyl is preferably a straight or branched $C_{2-6}$ alkynyl such as ethynyl, 1-propynyl, 2-propynyl or propargyl. The cycloalkenyl is a $C_{3-8}$ cycloalkenyl, preferably $C_{4-6}$ cycloalkenyl, and includes 1-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, 1,4-cyclohexadienyl, and so on. The aryl is preferably $C_{6-11}$ aryl group such as phenyl, 1-naphthyl, 2-naphthyl, biphenyl or anthryl, phenyl and naphthyls being especially preferred. The aralkyl is preferably $C_{7-13}$ aralkyl such as benzyl, phenethyl, 2-phenylpropyl, 3-phenylpropyl, 1-naphthylmethyl, 2-naphthylmethyl or benzhydryl. The heterocyclic group includes, among others, 5- to 8-membered rings containing 1 to 5 hetero atoms each selected from among nitrogen (inclusive of the oxide form thereof), oxygen and sulfur atoms, for instance, and fused rings derived therefrom. Said heterocyclic group has its bonding position at one of the carbon atoms thereof. Such a group is, for example, 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl)-, 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidyl, benzopyranyl, 1,8-, 1,5-, 1,6-, 1,7-, 2,7- or 2,6-naphthyridyl, quinolyl or thieno[2,3-b]pyridyl. Five- or six-membered heterocyclic groups containing 1 to 4 hetero atoms each selected from among nitrogen and sulfur atoms, such as thienyl, thiazolyl, thiadiazolyl, triazolyl and tetrazolyl, are particularly preferred.

Among these groups as substituents $R^2$, the alkyl, alkenyl and alkynyl may have 1 to 3 substituents each selected from among cycloalkyl*, cycloalkenyl*, aryl*, heterocyclic group*, alkoxycarbonyl, acyl, oxo, halogen, cyano, hydroxy, alkoxy, aryl*oxy, acyloxy, carbamoyloxy, sulfoxy, alkylsulfonyloxy, aryl*sulfonyloxy, nitro, amino, carboxy, carbamoyl, alkylthiocarbonyl, mercapto, alkylthio, aminoalkylthio, acylaminoalkylthio, aralkyl*thio, aryl*thio, heterocycle*thio and quaternary ammonium*, among others. As substituted alkyl groups, there may also be used, for example, groups of the formula

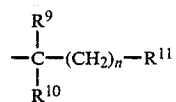

wherein n is an integer of 0 to 3, $R^9$ and $R^{10}$ are the same or different and each is hydrogen, alkyl, cycloalkyl*, aralkyl*, aryl*, heterocyclic group*, alkoxycarbonyl or acyl or $R^9$ and $R^{10}$ combined represent oxo, $R^{11}$ is hydrogen, alkyl, cycloalkyl*, aryl*, heterocyclic group*, halogen, cyano, hydroxy, alkoxy, aryl*oxy, aralkyl*oxy, acyloxy, carbamoyloxy, sulfoxy, alkylsulfonyloxy, aryl*sulfonyloxy, nitro, amino, azido, carboxy, alkoxycarbonyl, alkoxycarbonylalkyloxy, carbamoyl, alkylthiocarbonyl, acyl, mercapto, alkylthio, aminoalkylthio, acylaminoalkylthio, aralkyl*thio, aryl*thio, heterocycle*thio or quaternary ammonium*.

Referring to the substituent on the above-mentioned alkyl, alkenyl and alkynyl and to the groups $R^9$, $R^{10}$ and $R^{11}$, the alkoxy is preferably a straight or branched $C_{1-6}$ alkoxy such as methoxy, ethoxy, n-propoxy, isopropoxy, n-butoxy, isobutoxy, sec-butoxy, tert-butoxy, n-pentyloxy, isopentyloxy, n-hexyloxy or isohexyloxy. The halogen is fluorine, chlorine, bromine or iodine. The quaternary ammonium group includes, among others, quaternary ammonium groups of the general formula

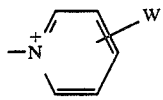

wherein W is a hydrogen atom or a methyl, carbamoyl, carboxyl, sulfoxy or methoxy group, which are derived from pyridine, carbamoyl-substituted pyridine (e.g. nicotinamide, isonicotinamide), carboxyl-substituted pyridine (e.g. nicotinic acid, isonicotinic acid), sulfoxy-substituted pyridine (e.g. pyridinesulfonic acid) and other pyridine derivatives, and quinolinium. The acyl moiety of acyl, acyloxy and acylaminoalkylthio group includes, among others, $C_{1-6}$ alkanoyl groups such as formyl, acetyl, propionyl, n-butyryl, isobutyryl, n-pentanoyl and n-hexanoyl, $C_{1-6}$ haloalkylcarbonyl groups such as monochloroacetyl, dichloroacetyl, trichloroacetyl and trifluoroacetyl, $C_{6-11}$ aryl*carbonyl groups such as benzoyl, 4-nitrobenzoyl, 4-hydroxybenzoyl, 4-methoxybenzoyl and 4-tert-butylbenzoyl, $C_{7-9}$ aralkyl*carbonyl such as phenylacetyl, 4-hydroxyphenylacetyl and 4-methoxyphenylacetyl, and 5- or 6-membered heterocyclecarbonyl groups or 5- or 6-membered heterocycleacetyl groups which contain at least one member of the class consisting of oxygen, nitrogen and sulfur atoms and may optionally be substituted, such as 2-thienylcarbonyl, 2-furylcarbonyl, 2-, 4- or 5-thiazolylacetyl, 2- or 3-thienylacetyl, 2- or 3-furylacetyl and 2-amino-4- or 5-thiazolylacetyl. The alkyl moiety of the alkylsulfonyloxy, alkylthiocarbonyl, alkylthio, aminoalkylthio, acylaminoalkylthio and alkoxycarbonylalkyloxy, the alkoxy moiety of the alkoxycarbonyl and alkoxycarbonylalkyloxy, the acyl moiety of the acyloxy and acylaminoalkylthio, the aryl moiety of the aryl*oxy, aryl*sulfonyloxy and aryl*thio, the heterocyclic group of the heterocycle*thio and the aralkyl moiety of the aralkyl*oxy and aralkyl*thio are as mentioned hereinabove.

As the substituents on the cycloalkyl, cycloalkenyl, aralkyl, aryl, heterocycle and quaternary ammonium, there may be mentioned among others alkyl, alkoxy, alkenyl, aryl, aralkyl, mercapto, alkylthio, arylthio, aralkylthio, alkylsulfonyl, arylsulfonyl, aralkylsulfonyl, haloalkyl, hydroxy, oxo, thioxo, halogen, nitro, amino, cyano, carbamoyl, carboxy, acyl, acyloxy, acylamino, hydroxyalkyl, carboxyalkyl, and mono- or dialkylaminoalkyl, (the alkyl, alkoxy, alkenyl, aryl, aralkyl, acyl and halogen being as mentioned hereinabove).

In the present invention, styryl is most preferable as a substituent R².

When an amino group occurs in the above-mentioned organic residue R² bonding through a carbon atom thereof, the amino group may be substituted or protected and a carboxyl, hydroxyl and/or thiol group, if present, may also be protected. The protective groups for such groups are appropriately selected from among those protective groups that are mentioned later herein.

The above-mentioned methyleneamine compound [III] can be produced in the conventional manner, for example, by subjecting an optically active α-amino acid such as mentioned below or a derivative thereof and an aldehyde to dehydration reaction.

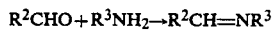

Thus, the substituent R³ in compounds [I], [I'] and [III] is the residue resulting from removal of the α-amino group from an optically active α-amino acid of the general formula R³NH₂ or a derivative thereof. The term "derivative of optically active α-amino acid" as used herein includes those to be mentioned later herein. R³NH₂ is, for example, D-aspartic acid, L-aspartic acid, D-asparagine, L-asparagine, D-glutamic acid, L-glutamic acid, D-glutamine, L-glutamine, D-alanine, L-alanine, D-arginine, L-arginine, D-cystathionine, L-cystathionine, D-cystine, L-cystine, D-histidine, L-histidine, D-homoserine, L-homoserine, D-isoleucine, L-isoleucine, D-lanthionine, L-lanthionine, D-leucine, L-leucine, D-lysine, L-lysine, D-methionine, L-methionine, D-norleucine, L-norleucine, D-norvaline, L-norvaline, D-ornithine, L-ornithine, D-serine, L-serine, D-threonine, L-threonine, D-tyrosine, L-tyrosine, D-thyronine, L-thyronine, D-valine, L-valine, D-phenylglycine, L-phenylglycine, D-phenylalanine or L-phenylalanine and is used either as it is or as a derivative of α-amino acid, for example, in the form of a di- or tripeptide. Such di- or tripeptide is described in detail later herein as an amide of α-amino acid. The "derivative of optically active α-amino acid" as described in this specification also includes derivatives of an optically active α-amino acid of the general formula R³NH₂ (R³ being as defined above) as resulting from substitution or protection of a functional group on the substituent R³ with an appropriate group. Thus, the functional group on the substituent R³ of the optically active α-amino acid as a starting material may be either in the free form or substituted or protected by an appropriate group. For instance, a carboxyl group on the substituent R³ may be in the esterified form resulting from substitution of its hydrogen with a group such as mentioned below. Such ester-forming group includes, among others, the above-mentioned alkyl*, cycloalkyl*, alkenyl*, alkynyl*, cycloalkenyl*, aryl* and aralkyl*, as well as methoxymethyl, ethoxymethyl, methylthiomethyl, 2-iodoethyl, 2,2,2-trichloroethyl, acetylmethyl, acetoxymethyl, pivaloyloxymethyl, propionyloxymethyl, 1,1-dimethylpropyl, 3-methyl-3-butenyl, 2-methylsulfonylethyl, mesylmethyl, 2-cyano-1,1-dimethylethyl, methylsulfinylmethyl, 2-(N,N-dimethylamino)ethyl, succinimidomethyl, phenacyl, benzyloxymethyl, trityl, 4-nitrobenzoylmethyl, 4-mesylbenzoylmethyl, phthalimidomethyl, 3,5-di-tert-butyl-4-hydroxybenzyl, benzenesulfonylmethyl, phenylthiomethyl, pyridine-1-oxido-2-methyl, bis(4-methoxyphenyl)methyl and further silyl groups of the general formula R⁵R⁶R⁷Si- (R⁵, R⁶ and R⁷ being as defined above), such as trimethylsilyl, triethylsilyl, tert-butyldimethylsilyl and tert-butyldiphenylsilyl. The carboxyl group may also be protected by conversion to other groups than the above-mentioned ester groups. As such groups other than esters, there may be mentioned those which form acid amide groups. Such acid amides include those having no substituent (i.e. those having the partial formula —CONH₂) and those whose hydrogen atom(s) is(are) substituted. Thus, these acid amides may be N-monosubstituted or N,N-disubstituted. N,N-Disubstituted amides also include amides derived from cyclic amines. The substituent of such amides is preferably C₁₋₆ alkyl, C₆₋₁₁ aryl, C₃₋₈ cycloalkyl. Specific examples of alkyl, aryl or cycloalkyl are as defined above. As the monosubstituted amide, there may be mentioned, for example, N-methylamide, N-ethylamide, N-phenylamide, etc. As the disubstituted amide, there may be mentioned, for example, N,N-dimethylamide, N,N-diethylamide, N-ethyl-N-methylamide, N-methyl-N-phenylamide, etc. As the cyclic amine in such amines as derived from cyclic amines, use is made of 5- to 7-membered secondary amines or, further, those having fused ring therewith. Specific examples of such cyclic amides are pyrrolidinamide, piperidinamide, morpholinamide, N'-methylpiperazinamide, 5,6-dihydrophenanthrenamide, etc. As the acid amide, in addition to the above acid amides, use is also made of amide derived from another α-amino acid, namely in the form of dipeptide and further in the form of tripeptide. As the α-amino acid which forms such dipeptides or tripeptides, there also may be mentioned optically active α-amino acid as described hereinabove. These α-amino acids are the same or different. In case an amino group other than the α-amino grup is existing on the above-mentioned substituent R³, said amino group may also be substituted or protected by a group such as mentioned below. As the substituent on the amino group, there may be mentioned alkyl*, cycloalkyl*, aralkyl*, aryl*, heterocyclic*, amidino, aminomethylene, carbamoyl and sulfoxy groups (said alkyl*, cycloalkyl*, aralkyl*, aryl* and heterocyclic* groups being as defined above). The amino group, together with such substituents, may form a cyclic amino group such as pyrrolidino, piperidino, morpholino or piperazino. As the amino-protecting group, there may be used those mentioned hereinbefore that are used for the same purpose in the field of β-lactam and peptide synthesis. Furthermore, as the hydroxyl- or thiol-protecting group, there may be used any of the protective groups that are generally usable as the hydroxyl- or thiol-protecting groups in the field of β-lactam and organic chemistry. As such protective groups, there may be mentioned acyl group as described above as a substituent on the substituent $R^2$, arylsulfonyl or aliphatic sulfonyl group as described above as the amino-protecting group, oxycarbonyl group of the general formula R°OCO—, as well as alkyl* groups (alkyl* being as defined above) such as tert-butyl, benzyl, 4-nitrobenzyl, trityl, methoxymethyl, methylthiomethyl and 2-methoxyethoxymethyl, silyl groups of the general formula $R^5R^6R^7Si$— ($R^5$, $R^6$ and $R^7$ being as defined above), such as trimethylsilyl, triethylsilyl, tert-butyldimethylsilyl and tert-butyldiphenylsilyl, and pyranyl groups such as 2-tetrahydropyranyl and 4-methoxy-4-tetrahydropyranyl. The selection of the above-mentioned carboxyl-, amino-, hydroxyl-, thiol- and other protecting groups is not critical in the practice of the present invention.

The reaction conditions to be used in the process for the production of the compounds of formula [I] and [I'] by reacting the substituted acetic acid [II] or a reactive derivative thereof resulting from carboxyl group modification with the substituted methyleneamine compound [III], preferably in the presence of a base, are described below in detail. As the reactive carboxylic acid derivative corresponding to formula [II], there may be mentioned the corresponding carboxylic halide, carboxylic acid anhydride, mixed acid anhydride, active carboxylic acid ester and active thioester, among others. These reactive derivatives are mentioned below in more detail.

(1) Acid halides:
As the acid halide, acid chlorides and acid bromides, for instance, are used.

(2) Acid anhydrides:
As acid anhydride, there may be used mixed acid anhydrides with a monoalkyl carbonic acid, mixed acid anhydrides with an aliphatic carboxylic acid (e.g. acetic acid, pivalic acid, valeric acid, isovaleric acid, trichloroacetic acid), mixed acid anhydrides with an aromatic carboxylic acid (e.g. benzoic acid) and symmetric acid anhydrides, among others.

(3) Active amides:
As the active amide, there are used, for instance, amides with pyrazole*, imidazole*, benzotriazole* or the like.

(4) Active esters:
Those active esters that are usable for the same purpose in the field of β-lactam and peptide synthesis may all be used. Thus, for instance, diethoxyphosphoric acid esters, diphenoxyphosphoric acid esters and the like and esters with 1-hydroxy-1H-2-pyridone, N-hydroxysuccinimide, N-hydroxyphthalimide and the like may be used.

(5) Active thioesters:
As the active thioester, there may be used thioesters with 2-pyridyl*thiol, 2-benzthiazolyl*thiol or the like among others.

The starting materials to be used in the practice of the invention, namely compound [II] or a reactive derivative thereof and compound [III], all can be easily produced by a known method or a per se known method.

The base to be used in carrying out the above reaction includes, among others, aliphatic tertiary amines (e.g. trimethylamine, triethylamine, tri-n-propylamine, tri-n-butylamine, cyclohexyldimethylamine), cyclic tertiary amines (e.g. N-methylpiperidine, N-methylpyrrolidine, N-methylmorpholine), aromatic amines (e.g. pyridine, lutidine, γ-collidine) and other organic bases such as 1,8-diazabicyclo[5,4,0]undec-7-ene (DBU). The reaction is preferably carried out in an organic solvent in the presence of an aliphatic tertiary amine (e.g. triethylamine, tri-n-butylamine).

The solvent usable in conducting the reaction includes, among others, ethers such as dioxane, tetrahydrofuran, diethyl ether, tert-butyl methyl ether, ethylene glycol dimethyl ether and diisopropyl ether, esters such as ethyl acetate and ethyl formate, halogenated hydrocarbons such as chloroform, carbon tetrachloride, trichloroethylene, dichloromethane and 1,2-dichloroethane, hydrocarbons such as benzene, toluene and n-hexane, amides such as N,N-dimethylformamide and N,N-dimethylacetamide, and other common organic solvents such as acetonitrile and dimethyl sulfoxide, either alone or in the form of a mixed solvent. The reaction temperature is within the range of −78° C. to 50° C., preferably −78° C. to 0° C. After completion of the reaction, compounds [I] or [I'] can be obtained in an optically pure form by subjecting the reaction mixture to per se known methods of isolation and purification, such as solvent extraction, fractional recrystallization and chromatography.

The reaction between the compound of general formula [II] and the optically active compound of general formula [III] gives a mixture of two possible diastereomers of general formula [I] and [I'] in which the substituents in positions 3 and 4 of the β-lactam ring are in the cis relationship as expected. In the above addition-cyclization reaction, the optically active compound of formula [III] induces two new chiral centers in high optical yields in positions 3 and 4 of the product β-lactam ring. Furthermore, it has been found that appropriate selection of the amino acid ($R^3NH_2$), substituent or protective group on the functional group of the amino acid, reaction solvent and reaction temperature, among others, leads to preferential formation of one of the two isomers.

The two isomers [I] and [I'] are in diastereomeric relationship with each other. After removal of the substituent $R^3$ by the method described later herein, the compound [IV] derived from [I] and the compound [IV'] derived from [I'] are optical enantiomers with each other. Therefore, by combining the so-selected reaction conditions with the above isolation and purification methods, it becomes possible to isolate either of the compound of formula [I] and the compound of formula [I'] in an easy manner and in good yields and further to isolate both of the diastereomers separately in an efficient manner. For instance, the reaction of the imine compound [III] derived from D-valine methyl ester or L-valine methyl ester and cinnamaldehyde with 2-phthalimidoacetyl chloride, when conducted in a solvent having a dielectric constant of 4.5 to 50 (as measured at 20° C. and $10 \times 10^3$ CPS), such as methylene chloride, ethyl acetate, tetrahydrofuran, acetonitrile or N,N-dimethylformamide, gives an approximately 1:1 mixture of the compound of formula [I] (3S,4R in configuration) and [I'] (3R,4S in configuration) for both cases of the D and L form starting materials. Fractional recrystallization can isolate both of the (3S,4R) isomer and (3R,4S) isomer separately. On the other hand, when performed in a solvent with a dielectric constant of 0 to 4.5 as measured at 20° C. and 10×10³ CPS, such as carbon tetrachloride, trichloroethylene, the reaction with the imine compound prepared from D-valine methyl ester and cinnamaldehyde used as the starting material gives the (3S,4R) form preferentially while the (3R,4S) isomer is formed preferentially from the imine compound prepared from L-valine methyl ester and cinnamaldehyde. Each diastereomer can easily be isolated by fractional recrystallization. As for the reaction of the imine compound derived from aspartic acid dimethyl ester and cinnamaldehyde with 2-phthalimidoacetyl chloride, the use of the imine compound from D-asparatic acid dimethyl ester and cinnamaldehyde as the starting material leads to preferential formation of the (3S,4R) isomer and the use of the imine compound from L-aspartic acid dimethyl ester and cinnamaldehyde to preferential formation of the (3R,4S) isomer, irrespective of the dielectric constant of the solvent used. When the imine compound prepared from serine methyl ester tertbutyldimethylsilyl ether and cinnamaldehyde was used as the starting material, the results were similar to the case in which the imine compound from aspartic acid dimethyl ester and cinnamaldehyde was used as the starting material. On the contrary, the use, as the starting material, of the imine compound from an L-amino acid amide, such as L-alanine pyrrolidinamide or L-alanine (5,6-dihydrophenanthrene)amide, and cinnamaldehyde led to preferential formation of the (3S,4R) isomer in contrast with the case of the use of the imine compounds from the above-mentioned amino acid esters and cinnamaldehyde. While, in the above, the description has been directed to amino acid methyl esters and amides, similar phenomena to the above-mentioned are also encountered with other alkyl esters and amides of amino acids.

The compounds [I] or [I'] obtained in accordance with the invention can be converted to the compounds [IV] or [IV'] of the formula shown below by eliminating the substituent $R^3$ therefrom.

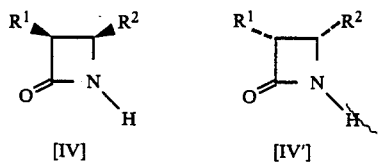

wherein $R^1$ and $R^2$ are as defined above.

The compounds [IV] are especially useful as intermediates for the synthesis of various β-lactam antibiotics such as a novel, broad-spectrum monobactam antibiotic (3S,4S)-3-[2-(2-amino-4-thiazolyl)-(Z)-2-(carboxymethoxyimino)acetamido]-4-carbamoyloxymethyl-2-azetidinone-1-sulfonic acid (hereinafter, "AMA-1080"), as mentioned later herein. Moreover, in the case of AMA-1080 synthesis, the use of such an intermediate can reduce the number of reaction steps required as compared with the known synthetic method starting with L-ascobic acid. Conversion of the compound [IV] to AMA-1080 is described in detail afterward. Furthermore, the compounds [IV] or [IV'] can also be utilized in the production of carbapenems, carbacephems or isocephalosporins.

Prior to the step of preparing a compound [IV] or [IV'] by elimination of the substituent $R^3$ from compound [I] or [I'], the functional group-protecting group or groups contained in compound [I] or [I'], if any, may be eliminated in advance. The protective group elimination can be effected in a per se known method. If desired, in particular, when the amino-protecting group in the substituent $R^1$ is affected or decomposed during the $R^3$ elimination reaction, protective group exchange may optionally be performed. Thus, the compounds [IV] or [IV'] can be produced by eliminating the amino-protecting group in the substituent $R^1$, introducing a new protecting group to the amino group of the resulting 3-amino compound of the general formula [V] or [V']

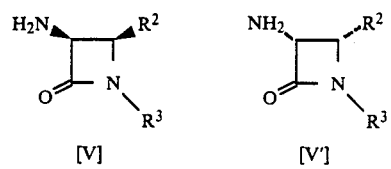

wherein $R^2$ and $R^3$ are as defined above, according to the conventional technique such as described later herein, and subjecting the thus-prepared compound [I] or [I'] bearing a new protective group on the amino group thereof to $R^3$ substituent elimination. Said new amino-protecting group is appropriately selected from among the above-mentioned amino-protecting groups. The compounds of general formula [V] or [V'] can be produced by converting the substituent $R^1$ in a compound of general formula [I] or [I'] to an amino group, and this conversion can be achieved in a per se known method. Thus, for example, a phthalimido group can be eliminated by reaction with a hydrazine reagent (e.g. hydrazine, methylhydrazine) or an amine reagent (e.g. N,N-dimethylpropanediamine), preferably in an inert organic solvent. The inert organic solvent usable in this reaction includes ethers such as dioxane, tetrahydrofuran, diethyl ether, diisopropyl ether and tert-butyl methyl ether, halogenated hydrocarbons such as chloroform, carbon tetrachloride, trichloroethylene, 1,2-dichloroethane and dichloromethane, and hydrocarbons such as n-hexane, benzene, toluene and xylene, among others. A substituent $R^4OCO—CH=C(CH_3)—NH—$ ($R^4$ being as defined above) can be converted to an amino group by hydrolysis under mild conditions, for instance.

While the elimination of the substituent $R^3$ from compounds [I] or [I'] can be effected by using the per se known method using lead tetraacetate (e.g. Tetrahedron Letters, 1973, 3851–3852), the present inventors have found out, in addition to said method, a method comprising converting the compound [I] or [I'] to the acid azide derivative followed by subjecting said derivative to the Curtius reaction and further a method comprising oxidative elimination of the substituent $R^3$ using a permanganate salt.

The conditions to be used in the above $R^3$ elimination methods are described below in detail. The method of eliminating the substituent $R^3$ using lead tetraacetate or by the Curtius reaction is generally applicable to the case where a free carboxyl group occurs in the substituent $R^3$. Therefore, if a protected carboxyl group is present in the substituent $R^3$, the carboxyl-protecting group is eliminated by a per se known method (e.g. hydrolysis as described hereinbelow) and the free carboxylic acid obtained is then subjected to reaction with lead tetraacetate or Curtius reaction. Thus, for instance, when the lead tetracetate method is employed, the compound [I] or [I'] having a free carboxyl group can be converted to an intermediate acetoxy derivative of the formula [VI] or [VI'] shown below by heating, under reflux, a mixture of 1 mole of compound [I] or [I'], 1 to 3 moles, preferably 1 to 1.2 moles, of lead tetraacetate and an appropriate catalyst (e.g. 0.01 to 0.2 mole of copper acetate) in an organic solvent for several minutes to several hours.

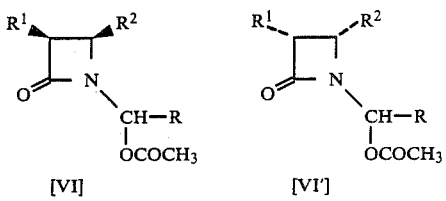

In the above formula, $R^1$ and $R^2$ are as defined above and R is the residue corresponding to an amino acid or a derivative thereof.

This reaction is preferably carried out under an inert gas (e.g. nitrogen gas, helium gas, argon gas). As the organic solvent mentioned above, there may be used ordinary organic solvents such as ethers (e.g. dioxane, tetrahydrofuran, diethyl ether, diisopropyl ether), esters (e.g. ethyl acetate, ethyl formate), halogenated hydrocarbons (e.g. chloroform, dichloromethane, 1,2-dichloroethane, 1,1,1-trichloroethane), hydrocarbons (e.g. benzene, toluene, n-hexane), amides (e.g. N,N-dimethylformamide, N,N-dimethylacetamide) and nitriles (e.g. acetonitrile), either alone or in the form of a mixed solvent. Some of the acetoxy derivatives [IV] or [IV'] thus obtained are unstable and may be converted to the compound [IV] or [IV'] during the solvent extraction and/or isolation and purification using a silica gel column. Preferably, however, further positive treatment of the acetoxy derivatives [VI] or [VI'] with a weak base such as potassium carbonate or a Lewis acid such as a silica gel column can give the compounds [IV] or [IV'] in better yields.

The method of eliminating the substituent $R^3$ using the Curtius reaction is mentioned below. The azidating agent for azidating the carboxyl group of a free carboxyl-containing compound [I] or [I'] is selected from among those azidating agents that are in general use but is preferably sodium azide or diphenylphosphoryl azide. The azidating agent can be reacted in an organic solvent with a carboxyl-reactive compound derived by conversion of the carboxyl group at the substituent $R^3$ to give acid azide [XI] or [XI'].

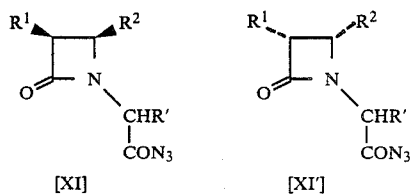

In the above formula, $R^1$ and $R^2$ are as defined above and CHR' is the residue remaining after removal of the α-amino and α-carboxyl groups from an optically active α-amino acid. Accordingly, $$\begin{array}{c} COR' \\ | \\ CON_3 \end{array}$$

corresponds to $R^3$ as defined hereinabove.

The carboxyl-derived reactive compounds derived from the compound [I] or [I'] include, among others, the above-mentioned acid halides, acid anhydrides, active amides, active esters and active thioesters. The azidation reaction is preferably carried out in the presence of a base, and the base is appropriately selected from among those organic bases mentioned hereinabove, preferably aliphatic tertiary amines such as triethylamine and tri-n-butylamine. In carrying out this method, the azidating agent is used generally in an amount of 1 to 1.5 moles per mole of the carboxylic acid, although it may be used in greater excess if the reaction is not disturbed thereby. The amount of the base depends on the starting materials and reaction conditions but generally is within the range of 1 to 3 moles, preferably 1 to 1.2 moles, per mole of the carboxylic acid. As the solvent in carrying out this reaction, there may be used ordinary organic solvents such as ethers (e.g. dioxane, tetrahydrofuran, diethyl ether, diisopropyl ether), esters (e.g. ethyl acetate, ethyl formate), halogenated hydrocarbons (e.g. chloroform, dichloromethane, 1,2-dichloroethane, 1,1,1-trichloroethane), hydrocarbons (e.g. benzene, toluene, n-hexane), amides (e.g. N,N-dimethylformamide, N,N-dimethylacetamide) and nitriles (e.g. acetonitrile), either alone or in the form of a mixed solvent. When the above-mentioned bases were liquid, they may also serve as the solvents. As far as the reaction can proceed, the reaction temperature is not critical. Generally, the reaction is performed at −50° C. to 150° C., preferably −30° C. to 80° C. The reaction is complete generally in tens of minutes to scores of hours (preferably 10 minutes to 5 hours) depending on the starting materials used, base, reaction temperature and solvent. In some instances, it takes scores of days (e.g. 2 to 3 days) for the reaction to be complete.

Although the acid azide thus produced may be isolated, the acid azide as formed is preferably dissolved in an organic solvent, heated and treated with an acid, followed by silica gel column chromatography, whereby the compound [IV] or [IV'] can be collected. The heating is conducted at 30° to 80° C., preferably in a refluxing solvent. The solvent to be used here includes those solvents mentioned above for use in conducting the azidation reaction. The acid is used generally in an amount of 1 to 10 moles per mole of the material to be treated therewith, and the acid itself may also serve as the solvent. The acid treatment is conducted for a period of 20 minutes to 3 hours, preferably about 30 minutes. The acid is appropriately selected from among inorganic acids such as hydrochloric acid, sulfuric acid and phosphoric acid, organic acids such as formic acid, acetic acid, trifluoroacetic acid and propionic acid and acidic ion exchange resins and the like. For obtaining the compounds [IV] or [IV'] from the corresponding acid azides, there may also be used, for example, a method comprising converting the acid azide first to the corresponding isocyanate e.g. by heating the acid azide in an organic solvent, then reaction the same with an alcohol and decomposing the urethane thus prepared. The reactions involved in the process just mentioned are all carried out using per se known techniques. The conversion of the acid azide to the isocyanate is conducted within the temperature range of 30° to 80° C., preferably in a refluxing solvent. The reaction period is 20 minutes to 3 hours, preferably about 30 minutes. The urethane compound is, for example, 2,2,2-trichloroethyl urethane or benzyl urethane. The reaction converting the isocyanate to the urethane is preferably effected by refluxing the isocyanate and an alcohol in an anhydrous organic solvent (e.g. diethyl ether, tetrahydrofuran, benzene). The 2,2,2-trichloroethyl urethane thus produced can be converted to the compound [IV] or [IV'], for example, by a method of reduction which comprises treating the urethane with zinc powder-hydrochloric acid at room temperature, and the benzyl urethane by ordinary catalytic reduction at room temperature, for instance. The method and reaction conditions for the conversion of the acid azide to the compound [IV] or [IV'] are not limited to those mentioned above.

The free carboxyl-containing compound [I] or [I'] is produced usually by hydrolyzing the corresponding ester or amide compound [I] or [I'] as mentioned hereinabove. Such hydrolysis is preferably effected by bases. As a base, frequent use may be made of alkali metal hydroxides (e.g. sodium hydroxide, potassium hydroxide) or alkali-earth metal hydroxides (e.g. calcium hydroxide, magnesium hydroxide. The reaction is usually carried out in a solvent, such as water or a mixed solvent consisting of water and an organic solvent. As such an organic solvent, use may be made of alcohols (e.g. methanol, ethanol), ketones (e.g. acetone, methyl ethyl ketone), nitriles (e.g. acetonitrile, benzonitrile) or amides (e.g. N,N-dimethylformamide, N,N-dimethylacetamide). The temperature ranges from 10° to 100° C., preferably 30° to 80° C. The reaction time is from 10 minutes to 10 hours, preferably 30 minutes to 2 hours. After the reaction is completed, the reaction mixture is neutralized by adding acid (e.g. hydrochloric acid, sulfuric acid) and concentrated. The free carboxylic acid can be obtained as crystals or as crude product through the known or per se known purification method.

The oxidative method of $R^3$ elimination using a permanganate is now described in detail. As the permanganate to be used in this reaction, potassium permanganate is preferred. The reaction is generally carried out in a solvent using 0.5 to 30 moles, preferably 1 to 10 moles, of the permanganate per mole of compound [I] or [I']. As the solvent, there may be used water and organic solvents in common use, such as ethers (e.g. dioxane, tetrahydrofuran, diethyl ether), esters (e.g. ethyl acetate, ethyl formate), halogenated hydrocarbons (e.g. carbon tetrachloride, chloroform, dichloromethane), hydrocarbons (e.g. benzene, toluene, n-hexane), amides (e.g. N,N-dimethylformamide, N,N-dimethylacetamide), alcohols (e.g. methanol, ethanol, isopropanol tert-butanol), dimethyl sulfoxide, sulfolane and hexamethylphosphoramide, either alone or in the form of a mixed solvent. Among these solvents, preferred are water, dioxane, tetrahydrofuran, carbon tetrachloride, dichloromethane, chloroform, benzene, N,N-dimethylformamide, N,N-dimethylacetamide, methanol, isopropanol and dimethyl sulfoxide. The use of a phase transfer catalyst in carrying out this reaction may result in better results. As used herein, the term "phase transfer catalyst" means a substance which promotes the reaction through solubilization of one of the reactants separately occurring in two liquid phases of a liquid-liquid system into the other liquid phase in the form of an ion pair. As such phase transfer catalyst, there may be used, for instance, those consisting of a cation composed of a nitrogen or phosphorus atom and four groups connected therewith and each selected from among alkyl, aryl and aralkyl groups (i.e. ammonium or phosphonium ion) and an acid residue (anion, e.g. $Cl^-$, $Br^-$, $I^-$, $F^-$, $ClO_4^-$, $BF_4^-$, $BH_4^-$, $HSO_4^-$, $OH^-$, $H_2PO_4^-$) and capable of achieving the object of this reaction.

More specifically, there may be used salts composed of a halide ion and an ammonium ion having four substituents which are the same or different and each is selected from among alkyl, aryl and aralkyl groups, for example tetraalkylammonium halides (total number of carbon atoms 4–50) such as tetramethylammonium chloride, tetraethylammonium chloride, tetra-n-butylammonium chloride, tri-n-octylmethyl-ammonium chloride, trimethylstearylammonium chloride, tetra-n-amylammonium bromide and n-hexyltrimethylammonium bromide, aryltrialkylammonium halides (total number of carbon atoms 9–50) such as phenyltrimethylammonium bromide, and aralkyltrialkylammonium halides (total number of carbon atoms 13–50) such as benzyldimethyldecylammonium chloride, benzyltriethylammonium chloride and cetylbenzyldimethylammonium chloride; salts composed of $HSO_4^-$ (hydrogen sulfate ion) and an ammonium ion having four substituents which are the same or different and each is selected from among alkyl, aryl and aralkyl groups, for example tetraalkylammonium hydrogen sulfates (total number of carbon atoms 4–50) such as tetra-n-butylammonium hydrogen sulfate and tetramethylammonium hydrogen sulfate; salts composed of $OH^-$ (hydroxide ion) and an ammonium ion having four substituents which are the same or different and each is selected from among alkyl, aryl and aralkyl groups, for example tetraalkylammonium hydroxides (total number of carbon atoms 16–50) such as tetra-n-butylammonium hydroxide; and salts composed of a halide ion and a phosphonium ion having four substituents which are the same or different and each is selected from among alkyl, aryl and aralkyl groups, for example tetraalkylphosphonium halides (total number of carbon atoms 4–50) such as tetra-n-butylphosphonium bromide, aralkyltriarylphosphonium halides (total number of carbon atoms 9–50) such as benzyltriphenylphosphonium chloride, and alkyltriarylphosphonium halides (total number of carbon atoms 19–50) such as n-butyltriphenylphosphonium bromide. Among these especially preferred are, for example, tri-n-octylmethylammonium chloride, tetra-n-butylammonium hydrogen sulfate, tetra-n-amylammonium bromide, benzyltriethylammonium chloride and tetra-n-butylphosphonium bromide. These phase transfer catalysts are used in an amount of 0.01 to 1 mole, preferably 0.05 to 0.2 mole, per mole of compound [I] or [I'] throughout the reaction period. As the solvent system for use with a phase transfer catalyst, preferred is a mixture of water and an organic solvent such as mentioned above. The reaction is carried out generally within the temperature range of 0° to 50° C. However, the temperature is not critical; heating or cooling may be made as necessary. An adequate reaction period may be chosen depending on the solvent, temperature and other factors. Generally, the reaction is complete in 1 to 24 hours. In some instances, the above elimination reaction may be accompanied by oxidation of the substituent group $R^2$.

The compounds [IV] and [IV'] obtained as a result of the above $R^3$ elimination reaction are known compounds and can be derived to the afore-mentioned AMA-1080 by a per se known series of reactions. For instance, oxidation of (3S,4R)-3-benzyloxycarbonylamino-4-styryl-2-azetidinone, which is obtained in the below-mentioned Example 33, with ozone followed by sodium borohydride gives (3S,4S)-3-benzyloxycarbonylamino-4-hydroxymethyl-2-azetidinone (Example 37) and reaction of the latter with chlorosulfonyl isocyanate gives (3S,4S)-3-benzyloxycarbonylamino-4-carbamoyloxymethyl-2-azetidinone [VII] (Example 38). This carbamoyloxymethyl compound [VII] is the same as the compound described in Japan Kokai Tokkyo Koho 59-46066 and AMA-1080 can be prepared therefrom by conducting a series of reactions described in said publication. The reaction series of the compound [VII] to AMA-1080 are illustrated, as follows.

yl-2-azetidinone-1-sulfonic acid sodium satl [IX]. Equimolar amount of the compound [IX] and (Z)-2-(2-amino-4-thiazolyl)-2-[(p-nitrobenzyloxycarbonylmethoxy)imino]acetic acid 2-benzothiazolyl thioester are suspended in anhydrous acetone and treated with 2.2 moles of triethylamine. Purification by chromatography affords (3S,4S)-3-(Z)-2-(2-amino-4-thiazolyl)-2-[(p-nitrobenzyloxycarbonylmethoxyimino)acetamido]-4-carbamoyloxymethyl-2-azetidinone-1-sulfonic acid triethylamine salt (X). Catalytic reduction of compound (X) in methanol in the presence of palladium supported by porous diatomaceous earth followed by treatment with sodium bicarbonate and chromatography gives AMA-1080 disodium salt.

The following examples are further illustrative of the present invention. It is to be noted, however, that they

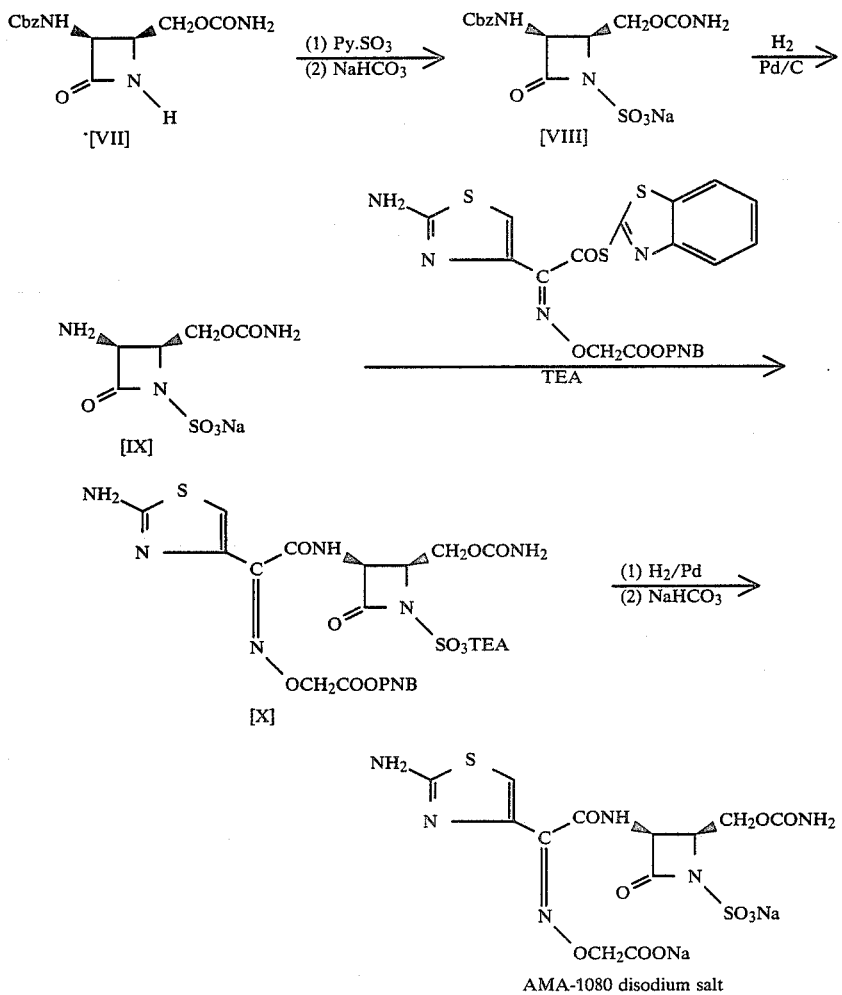

Cbz=benzyloxycarbonyl
Py=pyridine
PNB=p-nitrobenzyl
TEA=triethylamine

The reaction of compound [VII] with 2 moles of pyridine-sulfur trioxide complex at room temperature followed by treatment with sodium bicarbonate and chromatography gives (3S,4S)-3-benzyloxycarbonylamino-4-carbamoyloxymethyl-2-azetidinone-1-sulfonic acid sodium salt [VIII]. Catalytic reduction of compound [VIII] in the presence of palladium-carbon in anhydrous methanol gives (3S,4S)-3-amino-4-carbamoyloxymethare by no means limitative of the invention.

EXAMPLE 1

(a) To a solution of 3.35 g of L-valine methyl ester hydrochloride in 60 ml of dichloromethane is added 2.43 g of triethylamine with ice-cooling, and the mixture is stirred for 30 minutes, followed by removal of the solvent by distillation under reduced pressure. To the residue is added ethyl acetate and the insoluble material is filtered off. The filtrate is concentrated under reduced pressure. To the residue is added 40 ml of dichloromethane and the mixture stirred with 4.15 g of cinnamaldehyde and 3 g of anhydrous magnesium sulfate at room temperature for 2 hours. The insoluble material is filtered off and the filtrate is concentrated. The residue is dissolved in 40 ml of dichloromethane. Upon cooling at −70° C. to −60° C., 2.64 g of triethylamine is added and, with stirring, a solution of 4.48 g of 2-phthalimidoacetyl chloride in 20 ml of dichloromethane is added dropwise for 30 minutes. After the solution is warmed to room temperature, the reaction mixture is stirred for 1 hour and washed with water (twice), 1N hydrochloric acid and then with saturated aqueous sodium bicarbonate, successively. After drying the mixture over anhydrous magnesium sulfate, the solvent is distilled off to give 7 g of (3S,4R)/(3R,4S)-1-[(1S)-(1-methoxycarbonyl-2-methyl)propyl]-3-phthalimido-4-styryl-2-azetidinone. This product consists of an about 1:1 mixture of the (3S,4R) and (3R,4S) isomers. Recrystallization from methanol gives 2.1 g of (3S,4S) isomer as colorless needles. After concentration of the filtrate, the residue is recrystallized from diethyl ether-dichloromethane to give 1.9 g of (3R,4S) isomer as colorless prisms. The absolute configuration of the (3S,4R) isomer was determined by X-ray crystallographic analysis and the structures of the other isomers were determined in comparison with this (3S,4R) isomer.

(3S,4R) Isomer; M.p. 153.5°-154.5° C. IR $\nu_{max}^{KBr}$cm$^{-1}$: 1785 (shoulder), 1772, 1743, 1722, 1385, 1203, 980, 717.

NMR (ppm, CDCl$_3$) δ: 1.02(d, J=7 Hz, CH$_3$), 1.22(d, J=7 Hz, CH$_3$), 2.65(m, CH), 3.76(s, OCH$_3$), 3.85(d, J=9 Hz, CH), 4.62(dd, J=6,9 Hz, C$_4$—H), 5.57(d, J=6 Hz, C$_3$—H), 6.22(dd, J=9, 16 Hz, —C$\underline{H}$=CHPh), 6.62(d, J=16 Hz, —CH=C$\underline{H}$Ph), 7.22(s, aromatic protons), 7.60–7.93(m, aromatic protons).

Elemental analysis Calcd. for C$_{25}$H$_{24}$N$_2$O$_5$: C, 69.43; H, 5.59; N, 6.48%; Found: C, 69.41; H, 5.49; N, 6.53%. [α]$_D^{24}$−21.2° (C=0.645, methanol) [α]$_D^{23}$−20.2° (C=0.445, chloroform)

(3R,4S) Isomer; M.p. 124.5°-125.5° C.

IR $\nu_{max}^{KBr}$cm$^{-1}$: 1770-1780, 1720-1750, 1380, 1340, 1205, 979, 721.

NMR (ppm, CDCl$_3$) δ: 0.92(d, J=7 Hz, CH$_3$), 1.23(d, J=7 Hz, CH$_3$), 2.23(m, CH), 3.76(s, OCH$_3$), 4.32(d, J=9 Hz, CH), 4.98(dd, J=6,9 Hz, C$_4$—H), 5.58(d, J=6 Hz, C$_3$—H), 6.30(dd, J=9, 16 Hz, —C$\underline{H}$=CHPh), 6.72(d, J=16 Hz, —CH=C$\underline{H}$Ph), 7.23(s, aromatic protons), 7.60–7.93(m, aromatic protons).

Elemental analysis Calcd. for C$_{25}$H$_{24}$N$_2$O$_5$: C, 69.43; H, 5.59; N, 6.48%. Found: C, 69.52; H, 5.41; N, 6.46%. [α]$_D^{24}$+18.1° (C=0.770, methanol) [α]$_D^{23}$+44.5° (C=0.58, chloroform).

(b)-(h)

The isolated yields of 1-[(1S)-(1-methoxycarbonyl-2-methyl)propyl]-3-phthalimido-4-styryl-2-azetidinone and (3S,4R)-1-[(1S)-(1-methoxycarbonyl-2-methyl)propyl]-3-phthalimido-4-styryl-2-azetidinone under various addition-cyclization reaction conditions in the same manner as described in Example 1-(a) are shown in Table 1.

TABLE 1

L-Valine methyl ester → (8S,4R) + (8R,4S)

Ft = phthalimido, Sty = styryl

| | Solvent | Temperature (°C.) | Yield (%) | Ratio of (3S,4R):(3R,4S) | Isolated yield of (3S,4R)(%) |
|---|---|---|---|---|---|
| (b) | Carbon tetrachloride | −20~−25 | 74.0 | 2:5 | 12.5 |
| (c) | Tetrahydrofuran | −60~−70 | 41.6 | 9:10 | 10.5 |
| (d) | Ethyl acetate | −60~−70 | 76.8 | 7:8 | 24.0 |
| (e) | Acetonitrile | −20~−25 | 63.4 | 7:6 | 20.8 |
| (f) | Dichloromethane:N,N—dimethylformamide (1:1) | −60~−70 | 86.0 | 5:4 | 32.9 |
| (g) | Dichloromethane:Dimethylsulfoxide (1:1) | −60~−70 | 75.4 | 5:4 | 27.9 |
| (h) | N,N—Dimethylformamide | −60~−70 | 78.7 | 8:2 | 31.0 |

EXAMPLE 2

Starting from 7.59 g of L-valine benzylester, the similar reaction procedure described in Example 1-(a) gives 9.34 g of (3S,4R)/(3R,4S)-1-[(1S)-(1-benzyloxycarbonyl-2-methyl)propyl]-3-phthalimido-4-styryl-2-zaetidinone as an oil. The NMR spectrum shows that the product is an approximately 6:5 isomeric mixture IR $\nu_{max}^{Neat}$cm$^{-1}$: 2970, 1765, 1725, 1386.

(3R,4S) Isomer; NMR (ppm, CDCl$_3$)δ: 0.97(t, J=7 Hz, CH$_3$), 2.23(m, CH), 4.36(d, J=9 Hz, CH), 4.86(dd, J=6, 9 Hz, C$_4$—H), 5.20(s, CH$_2$), 5.52(d, J=6 Hz, C$_3$—H), 6.27(dd, J=9, 16 Hz, —C$\underline{H}$=CHPh), 6.57(d, J=16 Hz, —CH=C$\underline{H}$Ph), 7.20(s, aromatic protons), 7.37(s, aromatic protons), 7.53–7.90(m, aromatic protons).

(3S,4R) Isomer; NMR (ppm, CDCl$_3$)δ: 1.22(d, J=7 Hz, CH$_3$), 2.70(m, CH), 3.83(d, J=9 Hz, CH), 4.54(dd, J=6, 9 Hz, C$_4$—H), 5.20(s, CH$_2$), 5.50(d, J=6 Hz, C$_3$—H), 6.18(dd, J=9, 16 Hz, —C$\underline{H}$=CHPh), 6.57(d, J=16 Hz, —CH=C$\underline{H}$Ph), 7.20(s, aromatic protons), 7.37(s, aromatic protons), 7.53–7.90(m, aromatic protons).

EXAMPLE 3

With ice-cooling, 6.1 g of triethylamine is added to a solution of 8.4 g of D-valinemethyl ester hydrochloride in 100 ml of dichloromethane and the mixture is stirred for 30 minutes. The solvent is then distilled off under reduced pressure. To the residue is added ethyl acetate, and the insoluble material is filtered off. The filtrate is concentrated under reduced pressure. To the residue is added 100 ml of dichloromethane, and the mixture is stirred with 7.93 g of cinnamaldehyde and 30 g of anhydrous magnesium sulfate at room temperature for 3 hours. The magnesium sulfate is filtered off and the filtrate is concentrated under reduced pressure. The residue is dissolved in 200 ml of carbon tetrachloride and, on cooling at −16° C. to −17° C., 6.6 g of triethylamine is added, followed by dropwise addition of a solution of 11.5 g of 2-phthalimidoacetyl chloride in 200 ml of carbon tetrachloride with stirring for 40 minutes. After the solution is warmed to room temperature, the reaction mixture is stirred for an additional hour. To the reaction mixture is added 100 ml of dichloromethane and the mixture is washed with water, saturated aqueous sodium bicarbonate, 1N hydrochloric acid and water, successively, and dried over anhydrous magnesium sulfate. The solvent is then distilled off and the residue is washed with n-hexane to give 19 g of (3S,4R)/(3R,4S)-1-[(1R)-(1-methoxycarbonyl-2-methyl)propyl]-3-phthalimido-4-styryl-2-azetidinone as a solid. The NMR spectrum shows that the ratio of the (3S,4R) and (3R,4S) isomers is 73:27.

Two grams of the above-obtained solid dissolved in 20 ml of methanol are allowed to stand overnight to give crystals, which are washed with dichloromethane methanol (1:9, v/v) to obtain 541 mg of the (3S,4R) isomer. The filtrate is concentrated and the resulting residue is dissolved in 20 ml of methanol and the solution is allowed to stand at room temperature for 6 hours to obtain 210 mg of the (3R,4S) isomer as needles.

(3S,4R) Isomer; M.p. 124.5°-125.5° C.

IR $\nu_{max}^{KBr}$cm$^{-1}$: 1770-1780, 1720-1750, 1380, 1340, 1205, 979, 721.

NMR (ppm, CDCl$_3$)δ: 0.92(d, J=7 Hz, CH$_3$), 1.23(d, J=7 Hz, CH$_3$), 2.23(m, CH), 3.76(s, OCH$_3$), 4.32(d, J=9 Hz, CH), 4.98(dd, J=6, 9 Hz, C$_4$—H), 5.58(d, J=6 Hz, C$_3$—H), 6.30(dd, J=9, 16 Hz, —CH=CHPh), 6.72(d, J=16 Hz, —CH=CHPh), 7.23(s, aromatic protons), 7.60-7.93(m, aromatic protons), Elemental analysis Calcd. for C$_{25}$H$_{24}$N$_2$O$_5$: C, 69.43; H, 5.59; N, 6.48%. Found: C, 69.57; H, 5.64; N, 6.54%. [α]$_D^{24}$−17.9° (c=0.925, methanol), [α]$_D^{23}$−43.5° (c=0.8, chloroform)

(3R,4S) Isomer; M.p. 153.5°-154.5° C.

IR $\nu_{max}^{KBr}$cm$^{-1}$: 1785 (shoulder), 1772, 1743, 1722, 1385, 1203, 980, 717.

NMR (ppm, CDCl$_3$) δ: 1.02(d, J=7 Hz, CH$_3$), 1.22(d, J=7 Hz, CH$_3$), 2.65(m, CH), 3.76(s, OCH$_3$), 3.85(d, J=9 Hz, CH), 4.62(dd, J=6, 9 Hz, C$_4$—H), 5.57(d, J=6 Hz, C$_3$—H), 6.22 (dd, J=9, 16 Hz, —CH=CHPh), 6.62(d, J=16 Hz, —CH=CHPh), 7.22(s, aromatic protons), 7.60-7.93(m, aromatic protons).

Elemental analysis Calcd. for C$_{25}$H$_{24}$N$_2$O$_5$: C, 69.43; H, 5.59; N, 6.48%. Found: C, 69.41; H, 5.61; 6.53%. [α]$_D^{24}$+21.4° (c=0.770, methanol) [α]$_D^{23}$+21.5° (c=0.545, chloroform).

EXAMPLE 4

To a solution of 5.93 g of dimethyl D-aspartate hydrochloride in 50 ml of water are added 50 ml of saturated aqueous sodium chloride and 2.53 g of sodium bicarbonate and the mixture is extracted four times with chloroform. The extract is dried over anhydrous magnesium sulfate and concentrated under reduced pressure. To the residue are added 5.95 g of cinnamaldehyde and 100 ml of dichloromethane, followed by addition of 10 g of anhydrous magnesium sulfate. The mixture is stirred at room temperature for 1.5 hours. The insoluble material is filtered off and the filtrate is concentrated under reduced pressure. The residue is dissolved in 200 ml of trichloroethylene and, on cooling at −70° C., 3.34 g of triethylamine is added, followed by dropwise addition of a solution of 7.38 g of 2-phthalimidoacetyl chloride in 100 ml of trichloroethylene over 2 hours. The mixture is stirred at the same temperature for 30 minutes, then gradually warmed to room temperature. After being stirred further for 30 minutes, the reaction mixture is poured into an ice water. The organic layer is separated and the aqueous layer is extracted twice with dichloromethane. The combined organic layer is washed with aqueous sodium bicarbonate and dried over anhydrous magnesium sulfate. The solvent is then distilled off and 120 ml of diethyl ether is added to the residue. The mixture is allowed to stand overnight. The resulting crystalline precipitate is collected by filtration, washed with diethyl ether and dried to give 8.237 g of (3S,4R)-1-[(1R)-1,2-di(methoxycarbonyl)ethyl]-3-phthalimido-4-styryl-2-azetidinone. From the mother liquor is obtained 3.64 g of a 3:7 mixture of the (3S,4R) and (3R,4S) isomers.

(3S,4R) Isomer; M.p. 141°-142° C.

IR $\nu_{max}^{KBr}$cm$^{-1}$: 1785 (shoulder), 1775 (shoulder), 1763, 1743, 1720, 1395.

NMR (ppm, CDCl$_3$) δ: 3.61(s, OCH$_3$), 3.82(s, OCH$_3$), 4.87(dd, J=5.5, 9 Hz, C$_4$—H), 5.00 (t, J=7 Hz, CH), 5.628d, J=5.5 Hz, C$_3$—H), 6.18 (dd, J=9, 17 Hz, —CH=CHPh), 6.63(d, J=17 Hz, —CH=CHPh), 7.5-7.9(m, aromatic protons).

Elemental analysis Calcd. for C$_{25}$H$_{22}$N$_2$O$_7$: C, 64.93; H, 4.79; N, 6.06%. Found: C, 64.82; H, 4.91; N, 6.07%. [α]$_D^{24}$−49.6° (c=1.015, chloroform)

EXAMPLE 5

(a) Starting from dimethyl L-aspartate hydrochloride, the similar procedure described in Example 4 to give (3R,4S)-1-[(1S)-1,2-di(methoxycarbonyl)ethyl]-3-phthalimido-4-styryl-2-azetidinone.

(3R,4S) Isomer; M.p. 138°-140° C. IR $\nu_{max}^{KBr-1}$: 1760, 1740, 1720, 1390.

NMR (ppm, CDCl$_3$) δ: 3.61(s, OCH$_3$), 3.82(s, OCH$_3$), 4.87(dd, J=5.5, 9 Hz, C$_4$—H), 5.00(t, J=7 Hz, CH), 5.62(d, J=5.5 Hz, C$_3$—H), 6.18(dd, J=9, 17 Hz, —CH=CHPh), 6.63(d, J=17 Hz, —CH=CHPh), 7.1-7.9(m, aromatic protons).

Elemental analysis Calcd. for C$_{25}$H$_{22}$N$_2$O$_7$: C, 64.93; H, 4.79; N, 6.06%. Found: C, 65.01; H, 4.69; N, 6.03%. [α]$_D^{24.5}$+51.5 (c=0.955, chloroform)

(3S,4R) Isomer;

NMR (ppm, CDCl$_3$) δ: 3.21(d, J=7 Hz, CH$_3$), 3.77(s, OCH$_3$), 4.58(t, J=7 Hz, CH$_3$), 3.77(s, OCH$_3$), 4.58(t, J=7 Hz, CH), 4.73(dd, J=5.5, 9 Hz, C$_4$—H), 5.56(d, J=5.5 Hz, C$_3$—H), 6.18(dd, J=9, 17 Hz, —CH=CHPh), 6.65(d, J=17 Hz, —CH=CHPh), 7.1-7.9(m, aromatic protons).

(b)-(f)

The isolated yields of 1-[(1S)-1,2-di(methoxycarbonyl)ethyl]-3-phthalimido-4-styryl-2-azetidinone and the ratios of the (3S,4R) and (3R,4S) isomers under various addition-cyclization reaction conditions in the same manner as described in above Example 5-(a) are shown in Table 2.

TABLE 2

L-Aspartic acid dimethyl ester → (8S,4R) + (8R,4S)

| L-Aspartic acid dimetyl ester m mol | Cinnamaldehyde m mol | 2-Phthalimioacetyl chloride m mol | Additive | Solvent | Temperature (°C.) | Yield (%) | (8S,4R):(8R,4S) |
|---|---|---|---|---|---|---|---|
| (b) 10 | 20 | 11 | — | Dichloromethane | −70 | 78 | 80:70 |
| (c) 8 | 6 | 8.8 | — | Carbon tetrachloride | −15 | 88 | 26:74 |
| (d) 8 | 6 | 8.8 | CuCl | Dichloromethane | −70 | 68 | 80:70 |
| (e) 8 | 6 | 8.8 | MgCl$_2$ | Dichloromethane | −70 | 78 | 29:71 |
| (f) 8 | 6 | 8.8 | CaCl$_2$ | Dichloromethane | −70 | 82 | 80:70 |

Ft = phthalimido,
Sty = styryl

EXAMPLE 6

Starting from L-alanine tert-butyl ester, the similar procedure described in Example 1 gives (3S,4R)/(3R,4S)-1[(1S)-(1-tert-butoxycarbonyl)-ethyl]-3-phthalimido-4-styryl-2-azetidinone in 74% yield. The ratio of the (3S,4R) and (3R,4S) isomers is 45:55, and purification by silica gel column chromatography [eluent: ethyl acetate-n-hexane (2:3, v/v)] gives the (3S,4R) and (3S,4S) isomers.

(3S,4R) Isomer;

NMR (ppm, CDCl$_3$) δ: 1.48(s, tert-Bu), 1.66(d, J=8 Hz, CH$_3$), 4.12(q, J=8 Hz, CH), 4.67(dd, J=5, 8 Hz, C$_4$—H), 5.52(d, J=5 Hz, C$_3$—H), 6.25(dd, J=8, 16 Hz, —CH=CHPh), 6.66(d, J=16 Hz, —CH=CHPh), 7.1–7.9(m, aromatic protons).

[α]$_D^{24}$+6.54° (c=0.81, chloroform)

(3R, 4S) Isomer;

NMR(ppm, CDCl$_3$) δ: 1.46(d, J=8 Hz, CH$_3$), 1.48(s, tert-Bu), 4.63(q, J=8 Hz, CH), 4.96(dd, J=5, 9 Hz, C$_4$—H), 5.58(d, J=5 Hz, C$_3$—H), 6.26(dd, J=9, 16 Hz, —CH=CHPh), 6.67(d, J=16 Hz, —CH=CHPh), 7.1–7.9(m, aromatic protons).

[α]$_D^{24}$+14.8° (c=1.15, chloroform)

EXAMPLE 7

Starting from L-serine methyl ester tert-butyldimethylsilyl ether obtained from L-serine methyl ester hydrochloride and tert-butyldimethylsilyl chlorideimidazole, the similar procedure described in Example 1 gives (3R,4S)-[(1S)[1-methoxycarbonyl-2-(tert-butyldimethylsilyloxy)]ethyl]-3-phthalimido-4-styryl-2-azetidinone as a foam in 87% yield.

IR ν$_{max}^{KBr}$cm$^{-1}$: 1767, 1720, 1381, 1115, 835.

NMR(ppm, CDCl$_3$) δ: 0.80(s, tert-Bu), 3.78(s, OCH$_3$), 3.9–4.3(m, CH$_2$), 4.70(t, J=5 Hz, CH), 5.00(dd, J=5.5, 7 Hz, C$_4$—H), 5.65(d, J=5.5 Hz, C$_3$—H), 6.26(dd, J=7, 16 Hz, —CH=CHPh), 6.60(d, J=16 Hz, —CH=CHPh), 7.18(s, aromatic protons), 7.5–7.9(m, aromatic protons). [α]$_D^{25}$+22.1° (c=1.65, chloroform)

EXAMPLE 8

Starting from D-serine methyl ester tert-butyldimethylsilyl ether obtained from D-serine methyl ester hydrochloride and tert-butyldimethylsilyl chlorideimidazole, the similar procedure described in Example 1 gives (3S,4R)-1-[(1R)-[1-methoxycarbonyl-2-(tert-butyldimethylsilyloxy)]ethyl]-3-phthalimido-4-styryl-2-azetidinone as a foam in 90% yield.

IR ν$_{max}^{film}$cm$^{-1}$: 1760, 1720, 1482, 1380, 1250, 1120, 840.

NMR(ppm, CDCl$_3$)δ: 0.82(s, tert-Bu), 3.76(s, OCH$_3$), 3.9–4.3(m, CH$_2$), 4.73(t, J=5 Hz, CH), 5.03(dd, J=5.5, 7 Hz, C$_4$—H), 5.66(d, J=5.5 Hz, C$_3$—H), 6.28(dd, J=7, 16 Hz, —CH=CHPh), 6.61(d, J=16 Hz, —CH=CHPh), 7.18(s, aromatic protons), 7.5–7.9(m, aromatic protons). [α]$_D^{25}$—23.2° (c=0.92, chloroform)

EXAMPLE 9

Starting from D-phenylglycine methyl ester hydrochloride the similar procedure described in Example 1 gives 1-[(1R)-(1-methoxycarbonyl-1-phenyl)methyl]-3-phthalimido-4-styryl-2-azetidinone in 55% yield. Purification by silica gel column chromatography [eluent-:ethyl acetate-n-hexane (2:3, v/v)], gives the (3S,4R) and (3S,4R) isomers in the ratio of 1:2.

(3S,4R) Isomer;

IR ν$_{max}^{KBr}$cm$^{-1}$: 1765, 1720, 1385, 1205.

NMR(ppm, CDCl$_3$)δ: 3.82(s, OCH$_3$), 5.05(dd, J=5, 9 Hz, C$_4$—H), 5.55(dd, J=9, 16 Hz, —CH=CHPh), 5.64(d, J=5 Hz, C$_3$—H), 5.83(s, CH), 6.28(d, J=16 Hz, —CH=CHPh), 6.7–7.9(m, aromatic protons).

[α]$_D^{24}$—124° (c=0.66, chloroform)

(3R, 4S) Isomer;

IR ν$_{max}^{KBr}$cm$^{-1}$: 1760, 1720, 1380, 1200.

NMR(ppm, CDCl$_3$)δ: 3.79(s, OCH$_3$), 4.42(dd, J=5, 9 Hz, C$_4$—H), 5.49(d, J=5 Hz, C$_3$—H), 5.66(s, CH), 6.40(d, J=16 Hz, —CH=CHPh), 6.49(dd, J=9, 16 Hz, —CH=CH—Ph), 7.1–7.9(m, aromatic protons). [α]$_D^{24}$+29.6° (c=1.57, chloroform)

EXAMPLE 10

(a) Starting from dimethyl L-glutamate hydrochloride, the similar procedure described in Example 1 gives (3S,4R)/3R,4S)-1-[(1S)-1,3-di(methoxycarbonyl)-propyl]-3-phthalimido-4-styryl-2-azetidinone in 61% yield. The NMR spectrum of this product shows that the ratio of the (3S,4R), and (3R,4S) isomers is 1:2.

(3S,4R) Isomer;

NMR(ppm, CDCl$_3$)δ: 3.55(s, OCH$_3$), 3.80(s, OCH$_3$), 5.00(dd, J=5.5, 9 Hz, C$_4$—H), 5.57(d, J=5.5 Hz, C$_3$—H), 6.63(d, J=16 Hz, —CH=CHPh), 7.23(s, aromatic protons), 7.6–7.9(m, aromatic protons).

(3R,4S) Isomer;

NMR(ppm, CDCl$_3$)δ: 3.63(s, OCH$_3$), 3.80(s, OCH$_3$), 4.69(dd, J=5.5, 9 Hz, C$_4$—H), 5.63(d, J=5.5 Hz, C$_3$—H), 6.68(d, J=16 Hz, —CH=C$\underline{\text{H}}$Ph), 7.23(s, aromatic protons), 7.6–7.9(m, aromatic protons).

(b) Starting from diethyl L-glutamate hydrochloride, the similar procedure described in Example 1 gives (3S,4R)/(3R,4S)-1-[(1S)-1,3-di(ethoxycarbonyl)propyl]-3-phthalimido-4-styryl-2-azetidinone. The NMR spectrum shows that the product is a 2:3 mixture of the (3S,4R) and (3R,4S) ismoers.

EXAMPLE 11

Starting from L-phenylalanine methyl ester hydrochloride, the similar procedure described in Example 1 gives (3S,4R)/(3R,4S)-1-[(1S)-(1-methoxycarbonyl-2-phenyl)ethyl]-3-phthalimido-4-styryl-2-azetidinone in 83% yield. The NMR spectrum of this product shows that the ratio of the (3S,4R) and (3R,4S) isomers is 3:2.

IR $\nu_{max}^{KBr}$cm$^{-1}$: 1763, 1720, 1385.

(3S,4R) Isomer;
NMR(ppm, CDCl$_3$)δ: 3.20–3.85(m, CH$_2$), 3.78(s, OCH$_3$), 4.30–4.87(m, C$_4$—H, CH), 5.43(d, J=5 Hz, C$_3$—H), 5.89(dd, J=9, 16 Hz, —C$\underline{\text{H}}$=CHPh), 6.42(d, J=16 Hz, —CH=C$\underline{\text{H}}$Ph), 7.00–7.47(m, aromatic protons), 7.57–7.90(m, aromatic protons).

(3R,4S) Isomer;
NMR(ppm, CDCl$_3$)δ: 3.20–3.85(m, CH$_2$), 3.75(s, OCH$_3$), 4.30–4.87 (m, C$_4$—H, CH), 5.52(d, J=5 Hz, C$_3$—H), 6.07(dd, J=9, 16 Hz, —C$\underline{\text{H}}$=CHPh), 6.58(d, J=16 Hz, —CH=C$\underline{\text{H}}$—Ph), 7.00–7.47(m, aromatic protons), 7.57–7.90(m, aromatic protons).

EXAMPLE 12

Starting from L-methionine methyl ester hydrochloride, the similar procedure described in Example 1 gives (3S,4R)/(3R,4S)-1-[(1S)-(1-methoxycarbonyl-3-methylthio)propyl]-3-phthalimido-4-styryl-2-azetidinone in 92% yield. The NMR spectrum of this product shows that the ratio of the (3S,4R) and (3R,4S) isomers is 2:3.

(3S,4R) Isomer;
NMR(ppm, CDCl$_3$)δ: 2.12(s, SCH$_3$), 3.79(s, OCH$_3$), 4.68(dd, J=5, 9 Hz, C$_4$—H), 5.59(d, J=5 Hz, C$_3$—H), 6.67(d, J=16 Hz, —CH=C$\underline{\text{H}}$—Ph), 7.1–7.9(m, aromatic protons).

(3R,4S) Isomer;
NMR(ppm, CDCl$_3$)δ: 2.10(s, SCH$_3$), 3.79(s, OCH$_3$), 5.00(dd, J=5, 9 Hz, C$_4$—H), 5.64(d, J=5 Hz, C$_3$—H), 6.71(d, J=16 Hz, —CH=C$\underline{\text{H}}$—Ph), 7.1–7.9(m, aromatic protons).

EXAMPLE 13

Starting from L-asparagine methyl ester, the similar procedure described in Example 1 gives (3S,4R)/(3R,4S)-1-[(1S)-(1-methoxycarbonyl-2-carbamoyl)ethyl]-3-phthalimido-4-styryl-2-azetidinone in 53% yield. The NMR spectrum of this product shows that the ratio of the (3S,4R) and (3R,4S) isomers is 2:3.

(3S,4R) Isomer;
NMR(ppm, CDCl$_3$)δ: 3.77(s, OCH$_3$), 4.60(dd, J=5, 9 Hz, C$_4$—H), 5.57(d, J=5 Hz, C$_3$—H), 6.12(dd, J=9, 16 Hz, —C$\underline{\text{H}}$=CH—Ph), 6.67(d, J=16 Hz, —CH=C$\underline{\text{H}}$—Ph), 7.1–7.9(m, aromatic protons).

(3R,4S) Isomer;
NMR(ppm, CDCl$_3$)δ: 3.79(s, OCH$_3$), 4.84(dd, J=5, 9 Hz, C$_4$—H), 5.60(d, J=5 Hz, C$_3$—H), 6.22(dd, J=9, 16 Hz, —C$\underline{\text{H}}$=CH—Ph), 6.67(d, J=16 Hz, —CH=C$\underline{\text{H}}$—Ph), 7.1–7.9(m, aromatic protons).

EXAMPLE 14

(a) A suspension of 1.39 g of N-benzyloxycarbonyl-L-alanine pyrrolidineamide in 30 ml of methanol is stirred vigorously for 100 minutes in a hydrogen gas stream in the presence of 1 g of 10% palladium-on-carbon. The catalyst is filtered off and the filtrate is concentrated. The residue is dissolved in 20 ml of dichloromethane, and 1.32 g of cinnamaldehyde and 2 g of anhydrous magnesium sulfate are added, followed by stirring at room temperature for 1 hour. After filtration, the filtrate is concentrated under reduced pressure, and the residue is dissolved in 20 ml of dichloromethane. Upon cooling at −70° C., 1.02 g of triethylamine is added to the solution and, then, a solution of 2.24 g of 2-phthalimidoacetyl chloride in 20 ml of dichloromethane is added dropwise over 50 minutes. After the solution is warmed to room temperature, the mixture is stirred for 30 minutes and poured into ice water. The organic layer is separated, and the aqueous layer is extracted with dichloromethane. The combined organic layer is dried over anhydrous magnesium sulfate. The solvent is evaporated off and the residue is purified by silica gel column chromatography, using ethyl acetate-n-hexane (1:1, v/v) or ethyl acetate as an eluent to give 1.766 g of (3S,4R)/(3R,4S)-1-[(1S)-{1-(1-pyrrolidine)carbonyl}ethyl]-3-phthalimido-4-styryl-2-azetidinone. The NMR spectrum shows that the product is a 74:26 mixture of the (3S,4R) and (3R,4S) isomers. The absolute configuration of this compound was determined by comparison (e.g. in the NMR spectrum) with the compound obtained in Example 15.

(3S,4R) Isomer;
NMR(ppm, CDCl$_3$)δ: 1.48(d, J=8 Hz, CH$_3$), 4.75(q, J=8 Hz, CH), 4.78(dd, J=5, 9 Hz, C$_4$—H), 5.57(d, J=5 Hz, C$_3$—H), 6.06(dd, J=9, 16 Hz, —C$\underline{\text{H}}$=CH—Ph), 6.61(d, J=16 Hz, —CH=C$\underline{\text{H}}$—Ph), 7.1–7.9(m, aromatic protons).

(3R,4S) Isomer;
NMR(ppm, CDCl$_3$)δ: 1.46(d, J=8 Hz, CH$_3$), 4.89(q, J=8 Hz, CH), 5.16(dd, J=5, 9 Hz, C$_4$—H), 5.57(d, J=5 Hz, C$_3$—H), 6.26(dd, J=9, 16 Hz, —C$\underline{\text{H}}$=CH—Ph), 6.72(d, J=16 Hz, —CH=C$\underline{\text{H}}$—Ph), 7.1–7.9(m, aromatic protons).

(b)–(i)

The isolated yields of 1-[(1S)-{1-(1-pyrrolidine)carbonyl}ethyl]-3-phthalimido-4-styryl-2-azetidinone and the ratio of the (3S,4R) and (3R,4S) isomers under various addition-cyclization reaction conditions in the same manner as described in Example 14-(a) are shown in Table 3.

TABLE 3

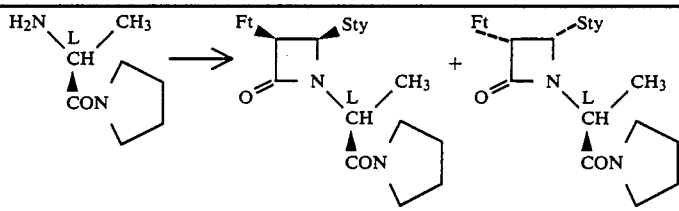

| | Acid amide m mol | Cinnnam-aldehyde m mol | 2-Phthalimidoacetyl chloride m mol | Solvent | Temperature (°C) | Additive | Yield (%) | (8S,4R):(8R,4S) |
|---|---|---|---|---|---|---|---|---|
| b | 2.5 | 5 | 5 | N,N—Dimetylformamide | −70 | — | 88 | 79:21 |
| c | 2.5 | 5 | 5 | Dichloromethane:N,N—Dimethyl-formamide (9:1) | −70 | — | 98 | 74:26 |
| d | 2.5 | 5 | 5 | Dichloromethane:Hexamethyl-phosphoramide (9:1) | −70 | — | 71 | 76:24 |
| e | 2.5 | 5 | 5 | Dichloromethane:MeNHCHO (9:1) | −70 | — | 41 | 74:26 |
| f | 2.5 | 5 | 5 | Nitromethane | −20 | — | 29 | 71:29 |
| g | 2.5 | 5 | 5 | N,N—Dimethylacetamide | −20 | — | 88 | 71:29 |
| h | 2.5 | 5 | 5 | N,N—Dimethylacetamide | −20 | $FeCl_3$ | 17 | 71:29 |
| i | 2.5 | 5 | 5 | N,N—Dimethylacetamide | −20 | $ZnCl_2$ | 74 | 72:28 |

Ft = phtalimide,
Sty = styryl

EXAMPLE 15

Starting from N-benzyloxycarbonyl-L-alanine(5,6-dihydrophenanthrene)amide, the similar procedure described in Example 14-(a) gives (3S,4R)/(3R,4S)-1-[(1S)-[1-[1-(5,6-dihydrophenanthridyl)]carbonyl]ethyl]-3-phthalimido-4-styryl-2-azetidinone in 82% yield. The NMR spectrum of this product shows that the ratio of the (3S,4R) and (3R,4S) isomers is 73:27. The absolute configuration of this compound is determined by comparison with the result obtained in Examples 30 and 35.

IR $\nu_{max}^{KBr}$cm$^{-1}$: 1763, 1720, 1668, 1383, 1200.

EXAMPLE 16

Starting from N-benzyloxycarbonyl-L-alanine (N-methyl aniline)amide, the similar procedure described in Example 14-(a) gives a mixture of two isomers of 1-[(1S)-{1-(N-methylanilino)carbonyl}ethyl]-3-phthalimido-4-styryl-2-azetidinone in 74% yield. The NMR of this product shows that the ratio of the two diastereomer is 63:37.

Diastereomer as the major product;
NMR(ppm, $CDCl_3$)δ: 1.49(d, J=7 Hz, $CH_3$), 3.27(s, $OCH_3$), 4.1–4.9(m, $C_4$—H, CH), 5.53(d, J=6 Hz, $C_3$—H), 6.23(dd, J=9, 16 Hz, —C$\underline{H}$=CH—Ph), 6.60(d, J=16 Hz, —CH=C$\underline{H}$—Ph), 7.1–8.0(m, aromatic protons).

Diastereomer as the minor product;
NMR(ppm, $CDCl_3$) δ: 1.27(d, J=7 Hz, $CH_3$), 3.22(s, $OCH_3$), 4.1–4.9(m, CH), 5.22(dd, J=6, 9 Hz, $C_4$—H), 5.48 (d, J=6 Hz, $C_3$—H), 6.23(dd, J=9, 16 Hz, —CH=CH—Ph), 6.70(d, J=16 Hz, —CH=C$\underline{H}$—Ph), 7.1–8.0(m, aromatic protons).

EXAMPLE 17

To a suspension of 1.18 g of pulverized D-valine in 1,2-dichloroethane (20 ml)-acetonitrile (4 ml) is added 1.66 g of tert-butyldimethylsilyl chloride, and the mixture is refluxed at 80° C. (bath temperature) for 4 hours and stirred at room temperature for 15 hours. To the reaction mixture is added 1.53 ml of triethylamine and the mixture is stirred for a while. The resulting crystals are collected by filtration and washed with 1,2-dichloroethane. The filtrate is concentrated under reduced pressure and the residue is dissolved in 30 ml of 1,2-dichloroethane. To this solution obtained above are added 2.65 g of cinnamaldehyde and 3 g of anhydrous magnesium sulfate and the mixture is stirred at room temperature for 2 hours. The insoluble material is filtered off and washed with 1,2-dichloroethane. The filtrate is concentrated under reduced pressure and the residue is dissolved in 50 ml of dichloromethane. Upon cooling at −70° C., 2.08 ml of triethylamine is added and then a solution of 2.69 g of 2-phtahlimidoacetyl chloride in 20 ml of dichloromethane is added dropwise over 1 hour. Thereafter, the mixture is allowed to stand at room temperature for 30 minutes and then the solution is gradually warmed to room temperature. The reaction mixture is poured into ice water and the dichloromethane layer is separated. The aqueous layer is extracted with dichloromethane. The combined dichloromethane layer is washed with aqueous sodium chloride and dried over anhydrous magnesium sulfate. The solvent is evaporated off under reduced pressure and the residue is dissolved in 50 ml of ethyl acetate, followed by addition of a solution of 0.5 g of potassium fluoride in 30 ml of water. The mixture is stirred for 1 hour and extracted twice with aqueous sodium bicarbonate. The extract is washed with diethyl ether and then adjusted to pH 1.5 with 5N hydrochloric acid, followed by extraction with ethyl acetate (twice). The organic layer is washed with aqueous sodium chloride, dried over anhydrous magnesium sulfate and concentrated under reduced pressure to give 3.3 g of 1-[(1R)-(1-carboxy-2-methyl)propyl]-3-phthalimido-4-styryl-2-azetidinone.

A solution of diazomethane in diethyl ether is added to a solution of 1 g of the product obtained above dissolved in 10 ml of ethyl acetate. The solvent is distilled off under reduced pressure and the residue is purified by silica gel column chromatography using ethyl acetate-n-hexane (1:1 then 2:3, v/v) as the eluent to give 0.873 g of (3S,4R)/(3R,4S)-1-[(1R)-(1-methoxycarbonyl-2-methyl)propyl]-3-phthalimido-4-styryl-2-azetidinone.

The integration curve in NMR spectrum shows that the (3S,4R)/(3R,4S) ratio is 72:28. The physical constants and characteristic properties of this product are in good agreement with those of the product obtained in Example 3.

EXAMPLE 18

Starting from L-valine, the similar procedure described in Example 17 gives (3S,4R)/(3R,5S)-1-[(1S)-(1-methoxycarbonyl-2-methyl)propyl]-3-phthalimido-4-styryl-2-azetidinone in 46% yield. The integration curve of this product in NMR spectrum shows that the ratio of the (3S,4R) and (3R,4S) isomers is 29:71.

EXAMPLE 19

Starting from N-benzyloxycarbonyl-L-valyl-L-valine methyl ester, the similar procedure described in Example 14 gives a mixture of two diastereomers of 1-[(1S)-[1-[{(1-(1S)-methoxycarbonyl-2-methyl)propyl-}aminocarbonyl]-2-methyl]propyl]-3-phthalimido-4-styryl-2-azetidinone in 87.5% yield. The NMR spectrum shows that the ratio of two diastereomers is 3:2.

IR $\nu_{max}^{KBr}$ cm$^{-1}$: 3380–3310, 2970, 1768–1740, 1725, 1678, 1387.

Diastereomer as the major product;

NMR (ppm, CDCl$_3$) δ: 0.85–1.40 (m, CH$_3$), 2.33–2.95 (m, CH), 3.07 (d, J=10 Hz, CH), 3.42 (s, OCH$_3$), 4.40–4.92 (m, C$_4$—H&CH), 5.62 (d, J=5 Hz, C$_3$—H), 6.31 (dd, J=9, 16 Hz, —CH=CH—Ph), 6.74 (d, J=16 Hz, —CH=CH—Ph), 7.05–7.40 (m, aromatic protons), 7.60–7.95 (m, aromatic protons).

Diastereomer as the major product;

NMR (ppm, CDCl$_3$) δ: 0.85–1.40 (m, CH$_3$), 2.33–2.95 (m, CH), 3.87 (d, J=10 Hz, CH), 3.40 (s, OCH$_3$), 4.40–4.92 (m, C$_4$—H&CH), 5.58 (d, J=5 Hz, C$_3$—H), 6.13 (dd, J=9, 16 Hz, —CH=CH—Ph), 6.67 (d, J=16 Hz, —CH=CHPh), 7.05–7.40 (m, aromatic protons), 7.60–7.95 (m, aromatic protons).

EXAMPLE 20

To a solution of 1.68 g of D-valine methyl ester hydrochloride in 15 ml of dichloromethane is added 1.66 ml of triethylamine with ice-cooling, and the mixture is stirred for 30 minutes. The solvent is then distilled off. The resulting residue is treated with ethyl acetate and, after removal of the insoluble material, the solvent is distilled off. The residue is dissolved in 30 ml of dichloromethane and, with ice-cooling, methyl glyoxylate (1.32 g) and 2 g of anhydrous magnesium sulfate are added, followed by stirring at room temperature for 2.5 hours. The insoluble material is filtered off and the filtrate is concentrated.

NMR (ppm, CDCl$_3$) δ: 0.91 (d, J=7 Hz, CH$_3$), 0.93 (d, J=7 Hz, CH$_3$), 2.38(sextet, J=7 Hz, CH), 3.72 (s, OCH$_3$), 3.86 (s, OCH$_3$), 7.69 (s, —CH=N—).

The residue is dissolved in 50 ml of trichloroethylene and, after addition of 2.08 ml of triethylamine with cooling at −78° C., a solution of 2.3 g of 2-phthalimidoacetyl chloride in 10 ml of trichloroethylene is added dropwise over 1 hour. After the solution is gradually warmed to room temperature, the reaction mixture is stirred for 1 hour. To the reaction mixture is added 50 ml of dichloromethane and the mixture is washed with water, diluted aqueous sodium bicarbonate, diluted hydrochloric acid and saturated aqueous sodium chloride, successively, and dried over anhydrous sodium sulfate. The solvent is then distilled off and the residue is purified by silica gel column chromatography to give 0.72 g of a mixture of two isomers of 1-[(1R)-(1-methoxycarbonyl-2-methyl)propyl]-3-phthalimido-4-methoxycarbonyl-2-azetidinone as an oil. The NMR spectrum shows that the product is a 3:2 mixture of two isomers.

IR $\nu_{max}^{film}$ cm$^{-1}$: 1770–1790, 1743 (shoulder), 1731, 1390, 1210, 909, 730, 718.

Diastereomer as the major product;

NMR (ppm, CDCl$_3$) δ: 1.03 (d, J=7 Hz, CH$_3$), 1.22 (d, J=7 Hz, CH$_3$), 2.3–3.0 (m, CH), 3.56 (s, OCH$_3$), 3.75 (s, OCH$_3$), 4.09 (d, J=8 Hz, CH), 4.60 (d, J=6 Hz, C$_4$—H), 5.62 (d, J=6 Hz, C$_3$—H), 7.6–8.0 (m, aromatic protons).

Diastereomer as the major product;

NMR (ppm, CDCl$_3$) δ: 0.96 (d, J=7 Hz, CH$_3$), 1.22 (d, J=7 Hz, CH$_3$), 1.22 (d, J=7 Hz, CH$_3$), 2.3–3.0 (m, CH), 3.53 (s, OCH$_3$), 3.75 (s, OCH$_3$), 4.09 (d, J=8 Hz, CH), 4.83 (d, J=6 Hz, C$_4$—H), 5.62 (d, J=6 Hz, C$_3$—H), 7.6–8.0 (m, aromatic protons).

EXAMPLE 21

(a) In a nitrogen gas stream, 1.5 g of methylhydrazine is added to a solution of 3.5 g of (3S,4R)-1-[(1S)-(1-methoxycarbonyl-2-methyl)propyl]-3-phthalimido-4-styryl-2-azetidinone obtained in Example 1 in 70 ml of dichloromethane, and the mixture is stirred at room temperature for 9 hours. The solvent is evaporated off under reduced pressure and the residue is redissolved in 70 ml of dichloromethane. The solution is allowed to stand at room temperature for 2 days. The insoluble material is filtered off and the filtrate is concentrated under reduced pressure. To the residue is added 70 ml of ethyl acetate and the mixture is washed with water and saturated aqueous sodium chloride and dried over anhydrous magnesium sulfate. The solvent is then distilled off under reduced pressure. To the residue are added 70 ml of dichloromethane and 2.4 g of 1,2-butylene oxide and, with ice-cooling and stirring, a solution of 2.4 g of benzyloxycarbonyl chloride in 10 ml of dichloromethane is added dropwise over 20 minutes. The mixture is stirred at room temperature for 1.5 hours and the solvent is distilled off under reduced pressure. To the residue is added diethyl ether to give crystals which are collected by filtration and dried to give 3.42 g of (3S,4R)-1-[(1S)-(1-methoxycarbonyl-2-methyl)propyl]-3-benzyloxycarbonylamino-4-styryl-2-azetidinone.

M.p.: 158.5°–160° C.

IR $\nu_{max}^{KBr}$ cm$^{-1}$: 1785 (shoulder), 1772, 1743, 1722, 1387, 1205.

NMR (ppm, CDCl$_3$) δ: 0.99 (t, J=7 Hz, CH$_3$), 2.45 (m, CH), 3.63 (s, OCH$_3$), 3.91 (d, J=9 Hz, CH), 4.50 (dd, J=5, 9 Hz, C$_4$—H), 5.04 (s, CH$_2$), 5.15 (dd, J=5, 8 Hz, C$_3$—H), 5.48 (br, d, J=8 Hz, NH), 6.08 (dd, J=9, 16 Hz, —CH=CH—Ph), 6.61 (d, J=16 Hz, —CH=CH—Ph), 7.21 (s, aromatic protons), 7.33 (s, aromatic protons).

Elemental analysis Calcd. for C$_{25}$H$_{28}$N$_2$O$_5$: C, 68.79; H, 6.47; N, 6.42%. Found: C, 68.84; H, 6.39; N, 6.42%. [α]$_D^{24}$ −20.7° (c=0.98, chloroform).

(b) (3R,4S)-1-[(1S)-(1-methoxycarbonyl-2-methyl)propyl]-3-phthalimido-4-styryl-2-azetidinone obtained in Example 1 is worked up in the same manner as described in Example 21-(a) to give (3R,4S)-1-[(1S)-(1-methoxycarbonyl-2-methyl)propyl]-3-benzyloxycarbonylamino-4-styryl-2-azetidinone in 92% yield.

M.p.: 130°–131.5° C.

IR $\nu_{max}^{KBr}$ cm$^{-1}$: 1790 (shoulder), 1770, 1720–1750, 1390, 1340, 980, 721.

NMR (ppm, CDCl$_3$)δ: 0.89 (d, J=7 Hz, CH$_3$), 1.01 (d, J=7 Hz, CH$_3$), 3.71 (s, OCH$_3$), 4.06 (d, J=9 Hz, CH), 4.72 (dd, J=5, 8 Hz, C$_4$—H), 5.10 (dd, J=5, 8 Hz, C$_3$—H), 6.15 (dd, J=9, 16 Hz, —CH=CH—Ph), 6.72 (d, J=16 Hz, —CH=CH—Ph), 7.21 (s, aromatic protons), 7.31 (s, aromatic protons).

Elemental analysis
Calcd. for C$_{25}$H$_{28}$N$_2$O$_5$: C, 68.79; H, 6.47; N, 6.42%; Found: C, 68.72; H, 6.53; N, 6.36%. [α]$_D^{24}$+31.3° (c=0.52, chloroform)

EXAMPLE 22

(a) To a solution of 0.856 g of (3S,4R)-1-[(1R)-(1-methoxycarbonyl-2-methyl)propyl]-3-phthalimido-4-styryl-2-azetidinone obtained in Example 3 in 10 ml of 1,2-dichloroethane is added 0.422 ml of methylhydrazine, and the mixture is allowed to stand at room temperature for 3 days. The insoluble material is filtered off and the filtrate is concentrated. The residue is dissolved in 10 ml of 1,2-dichloroehtane and, with ice-cooling and stirring, 2 ml of 1,2-butylene oxide is added, followed by dropwise addition of a solution of 0.41 g of benzyloxycarbonyl chloride in 3 ml of 1,2-dichloroethane over 30 minutes. After the solution is warmed to room temperature, the reaction mixture is stirred at the same temperature for 2 hours. The solvent is then distilled off under reduced pressure and water is added to the residue, followed by extraction with ethyl acetate. The extract is washed with aqueous sodium bicarbonate, diluted hydrochloric acid and water, successively, and dried over anhydrous magnesium sulfate. The solvent is distilled off and the residue is treated with n-hexane to give 0.76 g of (3S,4R)-1-[(1R)-(1-methoxycarbonyl-2-methyl)propyl]-3-benzyloxycarbonylamino-4-styryl-2-azetidinone.
M.p. 128°-129° C.
IR $\nu_{max}^{KBr}$ cm$^{-1}$: 1790 (shoulder), 1770, 1720-1750, 1390, 1340, 980, 721.
NMR (ppm, CDCl$_3$)δ: 0.89 (d, J=7 Hz, CH$_3$), 1.01 (d, J=7 Hz, CH$_3$), 3.71 (s, OCH$_3$), 4.06 (d, J=9 Hz, CH), 4.72 (dd, J=5, 9 Hz, C$_4$—H), 5.03 (s, CH$_2$), 5.10 (dd, J=5, 8 Hz, C$_3$—H), 5.68 (br, d, J=8 Hz, NH), 6.15 (dd, J=9, 16 Hz, —CH=CHPh), 6.72 (d, J=16 Hz, —CH=CH—Ph), 7.21 (s, aromatic protons), 7.31 (s, aromatic protons),
Elemental analysis Calcd. for C$_{25}$H$_{28}$N$_2$O$_5$: C, 68.79, H, 6.47; N, 6.42%. Found: C, 68.85, H, 6.48; N, 6.51%. [α]$_D^{24.5}$−29.6° (c−1.05, chloroform).

(b) (3R, 4S)-1-[(1R)-(1-Methoxycarbonyl-2-methyl)-propyl]-3-phthalimido-4-styryl-2-azetidinone obtained in Example 3 is worked up in the same manner as described in Example 22-(a) to give (3R,4S)-1-[(1R)-(1-methoxycarbonyl-2-methyl)propyl]-3-benzyloxycarbonylamino)-4-styryl-2-azetidinone in 89% yield.
M.p.: 160.5°-161.5° C.
IR $\nu_{max}^{KBr}$ cm$^{-1}$: 1785(shoulder), 1772, 1743, 1722, 1387, 1205.
NMR (ppm, CDCl$_3$) δ: 0.99 (t, J=7 Hz, CH$_3$), 2.2-2.6 (m, CH), 3.63 (s, OCH$_3$), 3.91 (d, J=9 Hz, CH), 4.50 (dd, J=5,9 Hz, C$_4$—H), 5.04 (s, CH), 5.15(dd, J=5,8 Hz, C$_3$—H), 5.77 (br.d, J=8 Hz, NH), 6.08 (dd, J=9, 16 Hz, —CH50 CHPh), 6.61 (d, J=16 Hz, —CH=CH—Ph), 7.21 (s, aromatic protons), 7.33 (s, aromatic protons). [α]$_D^{24}$+20.8° (c=0.72, chloroform)

EXAMPLE 23

The mixture of (3S,4R)- and (3R,4S)-1-[(1S)-(1-benzyloxycarbonyl-2-methyl)propyl]-3-phthalimido-4-styryl-2-azetidinone obtained in Example 2 is worked up in the same manner as described in Example 22-(a) to give (3S,4R)/(3R,4S)-1-[(1S)-(1benzyloxycarbonyl-2-methyl)propyl]-3-benzyloxycarbonylamino-4-styryl-2-azetidinonee in 98% yield.
IR $\nu_{max}^{Neat}$ cm$^{-1}$: 3300, 2970, 1760–1705, 1522, 1245.
(3S,4R) Isomer;
NMR (ppm, CDCl$_3$) δ:0.89 (d, J=7 Hz, CH$_3$), 1.02 (d, J=7 Hz, CH$_3$), 2.01–2.60 (m, CH), 4.04 (d, J=9 Hz, CH), 4.58 (dd, J=6.9 Hz, C$_4$—H), 5.03 (s, CH$_2$), 5.14 (s, CH$_2$), 5.40 (m, C$_3$—H), 6.05 (dd, J=9, 16 Hz, —CH=CHPh), 6.62 (d, J=16 Hz, —CH=CHPh), 7.21 (s, aromatic protons), 7.28 (s, aromatic protons), 7.33 (s, aromatic protons).
(3R,4S) Isomer;
NMR (ppm, CDCl$_3$) δ: 0.96 (t, J=7 Hz, CH$_3$), 2.01–2.60 (m, CH), 3.92 (d, J=9 Hz, CH), 4.45 (dd, J=6, 9 Hz, C$_4$—H), 5.03 (s, CH$_2$), 5.07 (s, CH$_2$), 5.40 (m, C$_3$—H), 6.00 (dd, J=9, 16 Hz, —CH=CHPh), 6.57 (d, J=16 Hz, —CH=CHPh), 7.21 (s, aromatic protons), 7.28 (s, aromatic protons), 7.33 (s, aromatic protons).

EXAMPLE 24

(3S,4R)-1-[(1R)-1,2-Di(methoxycarbonyl)ethyl]-3-phthalimido-4-styryl-2-azetidinone obtained in Example 4 is worked up in the same manner as described in Example 22-(a) to give (3S,4R)-1-[(1R)-1,2-di(methoxycarbonyl)ethyl]-3-benzyloxycarbonylamino)-4-styryl-2-azetidinone in 85% yield.
IR $\nu_{max}^{KBr}$ cm$^{-1}$: 1755, 1745, 1720.
NMR (ppm, CDCl$_3$) δ: 2.8–3.1 (m, CH$_2$), 3.54 (s, OCH$_3$), 3.75 (s, OCH$_3$), 4.64 (dd, J=5, 9 Hz, C$_4$—H), 4.75 (t, J=6 Hz, CH), 5.03 (s, CH$_2$), 5.19 (dd, J=5, 8 Hz, C$_3$—H), 6.10 (dd, J=9, 16 Hz, —CH=CHPh), 6.67 (d, J=16 Hz, —CH=CHPh), 7.31 (s, aromatic protons).
Elemental analysis Calcd. for C$_{25}$H$_{26}$N$_2$O$_7$: C, 64.37; H, 5.62; N, 6.01%. Found: C, 64.48; H, 5.73; N, 6.04%.

EXAMPLE 25

(3R,4S)-1-[(1S)-{1-Methoxycarbonyl-2-(tertbutyldimethylsilyloxy)}ethyl]-3-phthalimido-4-styryl-2-azetidinone obtained in Example 7 is worked up in the same manner as described in Example 22-(a) to give (3R,4S)-1-[(1S)-{1-methoxycarbonyl-2-(tert-butyldimethylsilyloxy)}ethyl]-3-benzyloxycarbonylamino-4-styryl-2-azetidinone in quantitative yield.
NMR (ppm, CDCl$_3$) δ: 0.82 (s, tert-Bu), 3.67 (s, OCH$_3$), 3.8–4.4 (m, CH$_2$), 4.49 (t, J=5 Hz, CH), 4.76 (dd, J=5, 7 Hz, C$_4$—H), 4.98 (s, CH$_2$), 5.23 (dd, J=5, 8 Hz, C$_3$—H), 6.20 (dd, J=7, 16 Hz, —CH=CHPh), 6.67 (d, J=16 Hz, —CH=CHPh), 7.15 (s, aromatic protons), 7.27 (m, aromatic protons).

EXAMPLE 26

(3S,4R)-1-[(1R)-{1-Methoxycarbonyl-2-(tertbutyldimethylsilyloxy)}ethyl]-3-phthalimido-4-styryl-2-azetidinone obtained in Example 8 is worked up in the same manner as described in Example 22-(a) to give (3S,4R)-1-[(1R)-{1-methoxycarbonyl-2-(tert-butyldimethylsilyloxy)}-ethyl]-3-benzyloxycarbonylamino-4-styryl-2-azetidinone in 90% yield.
NMR (ppm, CDCl$_3$) δ: 0.80 (s, tert-Bu), 3.67 (s, OCH$_3$), 3.8–4.2 (m, CH$_2$), 4.44 (t, J=5 Hz, CH), 4.72 (dd, J=5, 7 Hz, C$_4$—H), 4.98 (s, CH$_2$), 5.21 (dd, J=5, 8 Hz, C$_3$—H), 6.18 (dd, J=7, 16 Hz, —CH=CHPh), 6.65 (d, J=16 Hz, —CH=CH—Ph), 7.12 (s, aromatic protons), 7.23 (m, aromatic protons).

EXAMPLE 27

(3R,4S)-1-[(1R)-(1-Methoxycarbonyl-2-phenyl)methyl]-3-phthalimido-4-styryl-2-azetidinone obtained in Example 9 is worked up in the same manner as Example 21-(a) to give (3R,4S)-1-[(1-methoxycarbonyl-2-phenyl)methyl]-3-benzyloxycarbonylamino-4-styryl-2-azetidinone in 89% yield. In this product, the position 1 in the substituent at 1-position is racemized.

IR $\nu_{max}^{KBr}$ cm$^{-1}$: 1760–1720, 1240.

NMR (ppm, CDCl$_3$) δ: 3.65 3.72 (s, OCH$_3$), 5.00 (s, CH$_2$), 6.9–7.5 (m, aromatic protons).

EXAMPLE 28

Starting from 3.5 g of the 3:2 mixture of (3S,4R) and (3R,4S) isomers of 1-[(1S)-(1-methoxycarbonyl-2-phenyl)ethyl]-3-phthalimido-4-styryl-2-azetidinone obtained in Example 11, 1.34 g of methylhydrazine, 2.1 g of 1,2-butylene oxide and 1.9 g of benzyloxycarbonyl chloride, the similar procedure described in Example 21-(a) gives 3.3 g of the corresponding 3-benzyloxycarbonylamino compound. Addition of diethyl ether gives 1.8 g of crystals.

(IR $\nu_{max}^{KBr}$ cm$^{-1}$: 3310, 1770–1740, 1735–1750, 1520, 1260–1235).

The above crystals are recrystallized from dichloromethane (8 ml)-diisopropyl ether (40 ml) to give 1.52 g of (3S,4R)-[(1S)-(1-methoxycarbonyl-2-phenyl)ethyl]-3-benzyloxycarbonylamino-4-styryl-2-azetidinone.

M.P.: 133°–135° C.

IR $\nu_{max}^{KBr}$ cm$^{-1}$: 3270, 1755 (shoulder), 1738, 1720, 1535, 1275.

NMR (ppm, CDCl$_3$) δ: 3.34 (m, CH$_2$), 3.72 (s, OCH$_3$), 4.10 (dd, J=6, 9 Hz, CH), 4.35 (dd, J=5, 9 Hz, C$_4$—H), 5.00 (s, CH$_2$), 5.00–5.30 (m, C$_3$—H & NH), 5.50 (dd, J=9, 16 Hz, —CH=CHPh), 6.32 (d, J=16 Hz, —CH=CHPh), 7.20 (s, aromatic protons), 7.27 (s, aromatic protons), 7.05–7.45 (m, aromatic protons).

Elemental analysis Calcd. for C$_{20}$H$_{28}$N$_2$O$_5$: C, 71.89; H, 5.82; N, 5.78%. Found: C, 71.66; H, 5.79; N, 5.70%. $[\alpha]_D^{24}$ −74.7° (c=1.025, dichloromethane)

The corresponding (3R,4S) isomer is obtained from the filtrate as a foam.

NMR (ppm, CDCl$_3$) δ: 3.10–3.80 (m, CH$_2$), 3.71 (s, OCH$_3$), 4.31 (dd, J=5, 9 Hz, C$_4$—H), 4.51 (dd, J=6, 9 Hz, CH), 4.99 (s, CH$_2$), 5.00–5.20 (m, C$_3$—H), 5.45 (d, J=9 Hz, NH), 5.83 (dd, J=9, 16 Hz, —CH=CHPh), 6.61 (d, J=16 Hz, —CH=CH—Ph), 7.20 (s, aromatic protons, 7.27 (s, aromatic protons), 7.07–7.45 (m, aromatic protons).

EXAMPLE 29

The mixture of (3S,4R)- and (3R,4S)-1-[(1S)-(1-methoxycarbonyl-3-methylthio)propyl]-3-phthalimido-4-styryl-2-azetidinone obtained in Example 12 is worked up in the same manner as described Example 22-(a) to give 1-[(1S)-(1-methoxycarbonyl-3-methylthio)propyl]-3-benzyloxycarbonylamino-4-styryl-2-azetidinone as a 2:3 mixture of the (3S,4R) and (3R,4S) isomers.

(3S,4R) Isomer;

NMR (ppm, CDCl$_3$) δ: 2.04 (s, SCH$_3$), 3.66 (s, OCH$_3$), 5.02 (s, CH$_2$), 6.11 (dd, J=9, 16 Hz, —CH=CHPh), 6.62 (d, J=16 Hz, —CH=CHPh), 7.2–7.9 (m, aromatic protons).

(3R,4S) Isomer;

NMR (ppm, CDCl$_3$) δ: 1.97 (s, SCH$_3$), 3.70 (s, OCH$_3$), 5.02 (s, CH$_2$), 6.16 (dd, J=9, 16 Hz, —CH=CHPh), 6.68 (d, J=16 Hz, —CH=CH—Ph), 7.2–7.9 (m, aromatic protons).

EXAMPLE 30

The 73:27 mixture of the (3S,4R) and (3R,4S) isomers of 1-[(1S)-[1-{1-(5,6-dihydrophenanthridyl)}carbonyl]ethyl]-3-phthalimido-4-styryl-2-azetidinone obtained in Example 15 is worked up in the same manner as described in Example 22-(a) to give the corresponding 3-benzyloxycarbonylamino compound in 90.8% yield. Purification by silica gel column chromatography [eluent: ethyl acetate-n-hexane (2:3, v/v)] gives (3S,4R)- and (3R,4S)-1-[(1S)-[1-{1-(5,6-dihydrophenanthridyl)}carbonyl]ethyl]-3-benzyloxycarbonylamino-4-styryl-2-azetidinone each as a foam.

(3S,4R) Isomer;

IR $\nu_{max}^{KBr}$ cm$^{-1}$: 3340, 3300, 1755, 1720, 1666, 1390, 1221, 739, 695.

NMR (ppm, CDCl$_3$) δ: 1.31 (d, J=7 Hz, CH$_3$), 4.38 (q, J=7 Hz, CH), 4.97 (s, CH$_2$), 4.8–5.2 (m, C$_3$—H C$_4$—H), 5.3 (br. s, NH), 6.40 (d, J=16 Hz, —CH=CHPh), 6.8–7.9 (m, aromatic protons). $[\alpha]_D^{23}$ +4.31° (c=1.415, chloroform)

(3R,4S) Isomer;

IR $\nu_{max}^{KBr}$ cm$^{-1}$: 3300, 1750, 1719, 1660, 1382, 1220, 1183, 737, 687.

NMR (ppm, CDCl$_3$) δ: 1.21 (d, J=7 Hz, CH$_3$) 4.56 (q, CH), 5.00 (s, CH$_2$), 4.8–5.4 (m, C$_3$—H & C$_4$—H), 5.62 (d, J=8 Hz, NH), 6.00 (dd, J=8, 16 Hz, —CH=CHPh), 6.52 (d, J=16 Hz, —CH=CHPh), 7.0–7.9 (m, aromatic protons). $[\alpha]_D^{23}$ +105° (c=3.1, chloroform)

EXAMPLE 31

(3S,4R)-1-[(1S)-{1-(1-Pyrrolidine)carbonyl}ethyl]-3-phthalimido-4-styryl-2-azetidinone obtained in Example 14 is worked up in the same manner as described in Example 22-(a) to give (3S,4R)-1-[(1S)-{1-(1-pyrrolidine)carbonyl}ethyl]-3-benzyloxycarbonylamino-4-styryl-2-azetidinone as a foam in 92% yield.

NMR (ppm, CDCl$_3$) δ: 1.41 (d, J=7 Hz, CH$_3$), 1.4–2.2, 3.1–3.8 (m, CH$_2$), 4.3–4.7 (m, C$_4$—H & CH), 5.02 (s, CH$_2$), 5.10 (m, C$_3$—H), 5.94 (br. d, J=8 Hz, NH), 6.13 (dd, J=8, 16 Hz, —CH=CH—Ph), 6.63 (d, J=16 Hz, —CH=CHPh), 7.19 (s, aromatic protons), 7.27 (s, aromatic protons).

EXAMPLE 32

Starting from the 3:2 mixture of (3S,4R)- and (3R,4S)-1-[(1S)-[1-[{(1-(1S)-methoxycarbonyl-2-methyl)propyl}aminocarbonyl]-2-methyl]propyl]-3-phthalimido-4-styryl-2-azetidinone obtained in Example 19, the similar procedure described in Example 21-(a) gives 1-[(1S)-[1-[{(1-(1S)-methoxycarbonyl-2-methyl)propyl}aminocarbonyl]-2-methyl]propyl]-3-benzyloxycarbonylamino-4-styryl-2-azetidinone in 88.6% yield. The ratio of the (3S, 4R) and (3R, 4S) isomers of this product is 3:2. Addition of diethyl ether to this mixture gives the (3R,4S) isomer and this is recrystallized from dichloromethane-n-hexane. The (3S,4R) isomer is obtained from the filtrate as a foam.

(3S,4R) Isomer;

IR $\nu_{max}^{KBr}$ cm$^{-1}$: 3305, 2965, 1750–1718, 1670, 1525, 1255, 1210,

NMR (ppm, CDCl$_3$) δ: 0.85–1.17 (m, CH$_3$), 2.15–2.60 (m, CH), 3.35 (d, J=10 Hz, CH), 3.73 (s, OCH$_3$), 4.42–4.63 (m, C$_4$—H & CH), 5.07 (s, CH$_2$), 5.23 (dd, J=5, 9 Hz, C$_3$—H), 5.75 (d, J=9 Hz, NH), 6.07 (dd, J=9, 16 Hz, —CH=CHPh), 6.70 (d, J=16 Hz, —CH=CHPh), 7.24 (s, aromatic protons), 7.29 (s, aromatic protons), 7.46 (d, J=9 Hz, NH).

(3R,4S) Isomer; M.p.: 184°–185° C.

IR $\nu_{max}^{KBr}$ cm$^{-1}$: 3335, 3280, 1753, 1700, 1655, 1546, 1256, 1212.

NMR (ppm, CDCl$_3$) δ: 0.90 (t, J=6 Hz, CH$_3$), 0.95 (d, J=6 Hz, CH$_3$), 1.08 (d, J=6 Hz, CH$_3$), 2.20 (m, CH), 2.60 (m, CH), 3.42 (d, J=10 Hz, CH), 3.70 (s, OCH$_3$), 4.33–4.65 (m, C$_4$—H & CH), 5.07 (s, CH$_2$), 5.10 (dd, J=5, 9 Hz, C$_3$—H), 5.58 (d, J=9 Hz, NH), 6.07 (dd, J=9, 16 Hz, —CH=CHPh), 6.67 (d, J=16 Hz, —CH=CH—Ph), 6.98 (d, J=8 Hz, NH), 7.25 (s, aromatic protons), 7.32 (s, aromatic protons).

Elemental analysis Calcd. for C$_{30}$H$_{37}$N$_3$O$_6$: C, 67.27; H, 6.96; N, 7.84%. Found: C, 67.26; H, 7.13; N, 7.75%.

EXAMPLE 33

(a) With ice-cooling, 7.5 ml of water is added to a solution of 3.2 g of (3S,4R)-1-[(1S)-(1-methoxycarbonyl-2-methyl)propyl]-3-benzyloxycarbonylamino-4-styryl-2-azetidinone obtained in Example 21-(a) in 56 ml of acetone, and 9.9 ml of 1N NaOH is added dropwise to the solution over 1 hour. The mixture is stirred with ice-cooling for 3 hours and then at room temperature for 2 hours and adjusted to pH 2 by addition of 2N hydrochloric acid with ice-cooling. The acetone is distilled off under reduced pressure and the resulting crystals are dissolved in dichloromethane and washed with saturated aqueous sodium chloride. After drying over anhydrous magnesium sulfate, the solvent is distilled off, and diethyl ether-n-hexane is added to the mixture to give the corresponding carboxylic acid in quantitative yield. To a solution of 2.8 g of the above carboxylic acid in 100 ml of ethyl acetate are added 3.27 g of 90% lead tetraacetate and 0.132 g of cupric acetate monohydrate, and the atmosphere is substituted with nitrogen gas. The reaction mixture is refluxed under nitrogen for 1 hour, washed with water, saturated aqueous sodium bicarbonate (twice) and saturated aqueous sodium chloride, successively, and dried over anhydrous magnesium sulfate. The solvent is then distilled off. The resulting oil (partially crystals) is dissolved in 50 ml of ethyl alcohol and, with ice-cooling, 1.19 g of potassium carbonate and 0.55 g of 90% sodium borohydride are added, followed by stirring at room temperature for 2 hours. With ice-cooling, 1.6 g of acetic acid is added to the reaction mixture and the mixture is concentrated under reduced pressure. To the residue is added 50 ml of water and the resulting crystals are collected by filtration, washed with diethyl ether and dried to give 1.77 g of (3S,4R)-3-benzyloxycarbonylamino-4-styryl-2-azetidinone.

M.p.: 204°–207° C.

IR $\nu_{max}^{KBr}$ cm$^{-1}$: 3335, 1779, 1722, 1695, 1525, 1250.

NMR (ppm, DMSO-d$_6$) δ: 4.37(dd, J=5, 8 Hz, C$_4$—H), 5.00(dd, J=5, 9 Hz, C$_3$—H), 5.02(s, CH$_2$), 6.30(dd, J=8, 16 Hz, —CH=CH—Ph), 6.63(d, J=16 Hz, —CH=CH—Ph), 7.27(s, aromatic protons), 7.37(m, aromatic protons), 8.02(d, J=9 Hz, NH), 8.36(s, NH).

Elemental analysis Calcd. for C$_{19}$H$_{18}$N$_2$O$_3$: C, 70.79; H, 5.63; N, 8.69%. Found: C, 70.68; H, 5.72; N, 8.59%. [α]$_D^{24}$+65.8° (c=0.485, N,N-dimethylformamide)

(b) (3R,4S)-1-[(1S)-(1-Methoxycarbonyl-2-methyl)propyl]-3-benzyloxycarbonylamino-4-styryl-2-azetidinone obtained Example 21-(b) is worked up in the same manner as described in Example 33-(a) to give (3R,4S)-3-benzyloxycarbonylamino-4-styryl-2-azetidinone in 73.6% yield.

M.p.: 201°–204° C.

IR $\nu_{max}^{KBr}$ cm$^{-1}$: 3345, 1780, 1723, 1696, 1526, 1255.

NMR (ppm, DMSO-d$_6$) δ: 4.37(dd, J=5, 8 Hz, C$_4$—H), 5.00(dd, J=5, 9 Hz, C$_3$—H), 5.02(s, CH$_2$), 6.30(dd, J=8, 16 Hz, —CH=CH—Ph), 6.63(d, J=16 Hz, —CH=CH—Ph), 7.27(s, aromatic proton), 7.37(m, aromatic protons), 8.02(d, J=9 Hz, NH), 8.36(s, NH).

Elemental analysis Calcd. for C$_{19}$H$_{18}$N$_2$O$_3$: C, 70.79; H, 5.63; N, 8.69%. Found: C, 70.52; H, 5.61; N, 8.65%. [α]$_D^{24}$−64.9° (c=0.563, N,N-dimethylformamide).

(c) To a solution of 1.69 g of (3S,4R)-1-[(1-carboxyl-2-methyl)propyl]-3-benzyloxycarbonylamino-4-styryl-2-azetidinone obtained by the similar procedure as described in Example 33-(a) in 18 ml of dry tetrahydrofuran is added 0.5 g of triethylamine and, with stirring at −20° C., 0.5 g of ethyl chlorocarbonate is added, followed by stirring at −5° to −10° C. for 90 minutes. A solution of 0.315 g of sodium azide in 2 ml of water is added at the same temperature and the mixture is stirred at −5° to 0° C. for 30 minutes. The tetrahydrofuran is distilled off under reduced pressure and the residue is extracted with dichloromethane. The organic layer is separated, washed with saturated aqueous sodium chloride and dried over anhydrous magnesium sulfate. The solvent is then distilled off under reduced pressure to give 1.7 g of the corresponding azide compound as a foam. This product is dissolved in 50 ml of dry tetrahydrofuran and the solution is refluxed for 30 minutes. At 28° C., 4 ml of 1N hydrochloric acid is added and the mixture is stirred for 30 minutes. The tetrahydrofuran is distilled off under reduced pressure and the residue is extracted with dichloromethane. The extract is washed with saturated aqueous sodium chloride and dried over anhydrous magnesium sulfate. The solvent is then distilled off to give 1.3 g of the corresponding hydroxyl compound as a colorless foam. This product is purified by silica gel (30 g) column chromatography [eluent: ethyl acetate-n-hexane (1:1, v/v) or ethyl acetate] to give 0.9 g of (3S,4R)-3-benzyloxycarbonylamino-4-styryl-2-azetidinone.

(d) A solution of 1.7 g of the azide compound obtained in Example 33-(c) in 30 ml of dry benzene is refluxed for 30 minutes and, after addition of 1 ml of trichloroethanol, the mixture is refluxed for an additional hour. The benzene is distilled off under reduced pressure and the residue is purified by silica gel column chromatography [eluent: ethyl acetate-n-hexane (1:2, v/v)] to give 1.9 g of the corresponding trichloroethylurethane compound. To a solution of 0.2 g of this product in 4 ml of tetrahydrofuran is added 2 ml of 1N hydrochloric acid with ice-cooling and, after addition of 1.2 g of zinc powder with vigorous stirring, the reaction is allowed to proceed for 30 minutes. The zinc powder is filtered off and ethyl acetate and saturated aqueous sodium chloride are added to the filtrate, followed by phase separation. The ethyl acetate layer is washed with saturated aqueous sodium chloride and dried over anhydrous magnesium sulfate. The solvent is then distilled off under reduced pressure and the resulting hydroxyl compound is purified by silica gel column chromatography under the same conditions as above (c) to give 0.065 g of (3S,4R)-2-benzyloxycarbonylamino-4-styryl-2-azetidinone.

EXAMPLE 34

(a) (3S,4R)-1-[(1R)-(1-Methoxycarbonyl-2-methyl)-propyl]-3-benzyloxycarbonylamino-4-styryl-2-azetidinone obtained in Example 22-(a) is worked up in the same manner as described in Example 33-(a) to give (3S,4R)-3-benzyloxycarbonylamino-4-styryl-2-azetidinone in 78% yield.

(b) (3R,4S)-1-[(1R)-(1-Methoxycarbonyl-2-methyl)-propyl]-3-benzyloxycarbonylamino-4-styryl-2-azetidinone obtained in Example 22-(b) is worked up in the same manner as described in Example 33-(a) to give (3R,4S)-3-benzyloxycarbonylamino-4-styryl-2-azetidinone in 83% yield.

EXAMPLE 35

With stirring, 203 mg of ammonium cerium(IV) nitrate is added all at once to a solution of 62 mg of (3S,4R)-1-[(1S)-[1-[1-(5,6-dihydrophenanthridyl)]carbonyl]ethyl]-3-benzyloxycarbonylamino-4-styryl-2-azetidinone obtained in Example 30 in 2 ml of acetonitrile-water (4:1, v/v), and the mixture is stirred at room temperature for 30 minutes. To the reaction mixture is added diethyl ether-ethyl acetate and the resulting mixture is treated with 1N hydrochloric acid. The organic layer is washed with water and then with saturated aqueous sodium chloride and dried over anhydrous magnesium sulfate. The solvent is then distilled off to give 41 mg of (3S,4R)-1-[(1S)-(1-carboxyl)ethyl]-3-benzyloxycarbonylamino-4-styryl-2-azetidinone.

Thereafter, the similar procedure described in Example 33-(a) gives (3S,4R)-3-benzyloxycarbonylamino-4-styryl-2-azetidinone.

EXAMPLE 36

With stirring at room temperature, a solution of 0.467 g of (3S,4R)-1-[(1R)-1,2-di(methoxycarbonyl)ethyl]-3-benzyloxycarbonylamino-4-styryl-2-azetidinone in 20 ml of ethyl acetate and 0.068 g of n-Bu$_4$NHSO$_4$ are added to a solution of 0.79 g of potassium permanganate in 20 ml of water, and the mixture is stirred at room temperature for 2 hours. To the reaction mixture is added an aqueous solution of sodium thiosulfate and the mixture is passed through a Celite layer and washed with water and ethyl acetate. The aqueous layer is separated, adjusted to pH 1.5 with 5N hydrochloric acid and extracted twice with ethyl acetate. The extract is washed with aqueous sodium chloride and dried over anhydrous magnesium sulfate. The solvent is then distilled off under reduced pressure and the residue is purified by silica gel column chromatography [eluent: ethyl acetate-n-hexane (1:1 to 2:1, v/v)] to give 0.205 g of (3S,4R)-1-[(1R)-1,2-di(methoxycarbonyl)ethyl]-3-benzyloxycarbonylamino-4-methoxycarbonyl-2-azetidinone and 23 mg of (3S,4R)-3-benzyloxycarbonylamino-4-methoxycarbonyl-2-azetidinone.

(3S,4R)-1-[(1R)-1,2-Di(methoxycarbonyl)ethyl]-3-benzyloxycarbonylamino-4-methoxycarbonyl-2-azetidinone:

NMR (ppm, CDCl$_3$)δ: 2.8–3.2(m, CH$_2$), 3.53(s, OCH$_3$), 3.59(s, OCH$_3$), 3.71(s, OCH$_3$), 4.80(d, J=6 Hz, C$_4$—H), 4.84(t, J=6 Hz, CH), 5.08(s, CH$_2$), 5.42(dd, J=6, 10 Hz, C$_3$—H), 5.91(d, J=10 Hz, NH), 7.30(s, aromatic protons).

(3S,4R)-3-Benzyloxycarbonylamino-4-methoxycarbonyl-2-azetidinone:

NMR (ppm, CDCl$_3$) δ: 3.68(s, OCH$_3$), 4.42(d, J=5 Hz, C$_4$—H), 5.10(s, CH$_2$), 5.37(dd, J=5, 10 Hz, C$_3$—H), 6.10(d, J=10 Hz, NH), 6.82(s, NH), 7.31(s, aromatic protons).

EXAMPLE 37

In a mixture of 80 ml of methanol and 16 ml of dichloromethane is dissolved 0.8 g of (3S,4R)-3-benzyloxycarbonylamino-4-styryl-2-azetidinone obtained in Example 33 and, with cooling at −78° C., ozone gas is bubbled into the solution for 30 minutes. Thereafter, the excess ozone is purged with nitrogen and 0.19 g of sodium borohydride is added, followed by warming the solution to about 0° C. and stirring with ice-cooling for 30 minutes. To the mixture is added 0.3 g of acetic acid and the resulting mixture is concentrated under reduced pressure. To the residue are added ethyl acetate and water, and the ethyl acetate layer is separated. The aqueous layer is extracted with ethyl acetate and the combined ethyl acetate layer is washed with aqueous sodium chloride, dried over mangesium sulfate and concentrated under reduced pressure. The residue is crystallized from diethyl ether and the crystals are collected by filtration to give 0.5 g of (3S,4S)-3-benzyloxycarbonylamino-4-hydroxymethyl-2-azetidinone.

M.p.: 127°–128.5° C. [α]$_D$−22.0° (c=1.035, methanol)

IR ν$_{max}^{KBr}$ cm$^{-1}$: 3298, 1760(shoulder), 1710–1690, 1550, 1272, 1070.

Elemental analysis Calcd. for C$_{12}$H$_{14}$N$_2$O$_4$: C, 57.59; H, 5.64; N, 11.19%. Found: C, 57.55; H, 5.61; N, 11.01%.

EXAMPLE 38

In 16 ml of dry dichloromethane is dissolved 0.50 g of (3S,4S)-3-benzyloxycarbonylamino-4-hydroxymethyl-2-azetidinone obtained in Example 37 and, on cooling at −15° C., 0.368 g of chlorosulfonyl isocyanate is added, followed by stirring for 30 minutes. A 15-ml aqueous solution of 0.72 g of sodium sulfite is added and the solution is warmed to room temperature, followed by stirring for 1 hour. The dichloromethane is distilled off under reduced pressure and the residue is extracted twice with ethyl acetate-tetrahydrofuran (3:1, v/v). The extract is washed with aqueous sodium chloride, dried over mangesium sulfate and concentrated under reduced pressure. The residue is purified by silica gel column chromatography [eluent: chloroform-ethyl acetate-methanol (40:55:5, v/v/v)] to give 0.323 g of (3S,4S)-3-benzyloxycarbonylamino-4-carbamoyloxymethyl-2-azetidinone.

M.p.: 192°–193° C.

[α]$_D$+61° (c=1, methanol).

EXAMPLE 39

To 15 ml of chloroform is suspended 2.16 g of L-phenylalanine methyl ester hydrochloride and 10 ml of saturated aqueous sodium bicarbonate is added with vigorous stirring. The organic layer is separated and the aqueous layer is extracted twice with chloroform. After the combined organic layer is dried over anhydrous magnesium sulfate, the solvent is distilled off. The residue is dissolved in 50 ml of dichloromethane and the mixture is stirred with 1.99 g of cinnamaldehyde and 3 g of anhydrous magnesium sulfate at room temperature for one hour. The insoluble material is filtered off and the filtrate is concentrated to give a Schiff base. A solution of 4.2 g of N-benzyloxycarbonylglycine and 6.07 g triethylamine in 50 ml of dichloromethane is cooled to −40° C. and 6.52 g of ethyl chloroformate is added and stirred at −20° C. for 10 minutes. To the reaction mixture is added a solution of the above Schiff base and 1.52 g of triethylamine in 20 ml of chloroform and the mixture is stirred at room temperature for 2 hours. After the solvent is distilled off, the residue is dissolved in ethyl acetate and the organic layer is washed with 1N hydrochloric acid, aqueous sodium bicarbonate, saturated aqueous sodium chloride, successively. After drying the mixture over anhydrous magnesium sulfate, the solvent is distilled off and the residue is purified by silica gel column chromatography, using ethyl acetate-n-hexane (2:3, v/v) as an eluant to give 3.43 g of (3S,4R)/(3R,4S)-1-[(1S)-(1-methoxycarbonyl-2-phenyl)ethyl]-3-benzyloxycarbonylamino-4-styryl-2-azetidinone (ca. 50:50) as crystals. Recrystallization from ethyl acetate-n-hexane gives 1.3 g of (3S,4R) isomer as crystals. Melting point, IR spectrum, NMR spectrum and $[\alpha]_D$ of this product are in perfect agreement with those of the product obtained in Example 28.

EXAMPLE 40

Starting from 1.18 g of D-valine, the similar procedure as described in Example 17 gives 3.41 g of 1-[(1R)-(1-carboxy-2-methyl)propyl]-3-phthalimido-4-styryl-2-azetidinone as an oil, using as a reaction solvent trichloroethylene in place of dichloromethane. The NMR spectrum shows that the ratio of the (3S,4R) and (3R,4S) isomers is 85:15. This mixture is dissolved in 50 ml of diethyl ether and 2.11 g of dicyclohexylamine is added to give 3.15 g of dicyclohexylamine salt of the (3S,4R) isomer as crystals.

NMR(ppm, CDCl$_3$) δ: 0.9–2.5 (m,

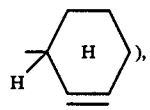

1.07 (d, J=7 Hz, CH$_3$), 1.22 (d, J=7 Hz, CH$_3$), 2.8–3.3 (m,

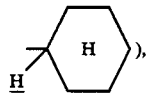

4.17 (d, J=9 Hz, CH), 5.16 (dd, J=5, 8 Hz, C$_4$—H), 5.53 (d, J=5 Hz, C$_3$—H), 6.36 (dd, J=8, 15 Hz, CH=CHPh), 6.62 (d, J=15 Hz, CH=CHPh), 7.22 (s, aromatic protons), 7.5–8.0 (m, aromatic protons).

EXAMPLE 41

Starting from 352 mg of D-valine, the similar procedure as described in Example 17 gives 1.36 g of (3S,4R)-1-[(1R)-(1-carboxy-2-methyl)propyl]-3-(4,5-diphenyl-2-oxo-4-oxazolin-3-yl)-4-styryl-2-azetidinone as a pale yellow oil, using 1.04 g of 2-(4,5-diphenyl-2-oxo-4-oxazolin-3-yl)-acetyl chloride in place of 2-phthalimidoacetyl chloride and as a reaction solvent trichloroethylene in place of dichloromethane. This product is dissolved in ethyl acetate and methylated with diazomethane to give 1.06 g of (3S,4R)-1-[(1R)-(1-methoxycarbonyl-2-methyl)propyl]-3-(4,5-diphenyl-2-oxo-4-oxazolin-3-yl)-4-styryl-2-azetidinone as crystals. The (3R,4S) isomer is not detected in the NMR spectrum and liquid chromatography of this product.

M.p.: 141°–142° C.

IR $\nu_{max}^{KBr}$ cm$^{-1}$: 1770, 1760, 1745.

NMR(ppm, CDCl$_3$) δ: 0.90 (d, J=7 Hz, CH$_3$), 1.17 (d, J=7 Hz, CH$_3$), 1.9–2.4 (m, CH), 3.68 (s, OCH$_3$), 4.30 (d, J=9 Hz, CH), 4.73 (d, J=5 Hz, C$_3$—H), 4.79 (dd, J=5, 8 Hz, C$_4$—H), 6.56 (dd, J=8, 16 Hz, CH=CHPh), 6.85 (d, J=16 Hz, CH=CHPh), 7.0–7.7 (m, aromatic protons)

$[\alpha]_D^{25} + 90.6°$ (c=0.48, chloroform)

EXAMPLE 42

To a solution of 1.19 g of N-benzyl-N-benzyloxycarbonylglycine in 10 ml of trichloroethylene is added dropwise under cooling at −10° C. 1.11 ml of triethylamine and then a solution of 845 mg of p-chlorobenzenesulfonyl chloride in 10 ml of trichloroethylene, successively. After stirred at the same temperature for 30 minutes, a solution of the Schiff base, which is prepared from the reaction between 336 mg of L-valine methyl ester hydrochloride and 397 mg of cinnamaldehyde, in 10 ml of trichloroethylene is added dropwise to the mixture for 15 minutes. After stirred at room temperature for 3 hours, the reaction mixture is concentrated and the residue is dissolved in ethyl acetate. The organic layer is washed with 1N hydrochloric acid, aqueous sodium bicarbonate and saturated aqueous sodium chloride, successively and dried over anhydrous magnesium sulfate. The solvent is evaporated off and the residue is purified by silica gel column chromatography, using n-hexane-ethyl acetate (7:3, v/v) as an eluant to give 1.06 g of a mixture of (3R,4S)- and (3S,4R)-1-[(1S)-(1-methoxycarbonyl-2-methyl)propyl]-3-(N-benzyl-N-benzyloxycarbonyl)amino-4-styryl-2-azetidinone (33:67, liquid chromatography) as an oil.

IR $\nu_{max}^{CHCl_3}$ cm$^{-1}$: 1757, 1735, 1698.

What we claim is:

1. An optically active β-lactam of the formula

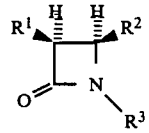

wherein $R^1$ is a protected amino group;

$R^2$ is (I) alkyl, alkenyl or alkynyl, such groups being unsubstituted or substituted by one to three substituents each selected from the class (A) consisting of (1) cycloalkyl*, (2) cycloalkenyl*, (3) aryl*, (4) heterocyclic* group selected from the class (H) consisting of 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidyl, benzopyranyl, 1,8-, 1,5-, 1,6-, 1,7-, 2,7- or 2,6-naphthyridyl, quinolyl and thieno[2,3-b]pyridyl, (5) alkoxycarbonyl, (6) acyl, (7) oxo, (8) halogen, (9) cyano, (10) hydroxy, (11) alkoxy, (12)

aryl*oxy, (13) acyloxy, (14) carbamoyloxy, (15) sulfoxy, (16) alkylsulfonyloxy, (17) aryl*sulfonyloxy, (18) nitro, (19) amino, (20) carboxy, (21) carbamoyl, (22) alkylthiocarbonyl (23) mercapto, (24) alkylthio, (25) aminoalkylthio, (26) acylaminoalkylthio, (27) aralkyl*thio, (28) aryl*thio and (29) heterocycle*thio wherein the heterocycle is one selected from the class (H) as defined above, the acyl moiety of acyl, acyloxy and acylaminoalkylthio in the above groups being a $C_{1-6}$ alkanoyl group, a $C_{1-6}$ haloalkylcarbonyl group, a $C_{6-11}$ aryl*carbonyl group, a $C_{7-9}$ aralkyl*carbonyl, 2-thienylcarbonyl, 2-furylcarbonyl, 2-, 4- or 5-thiazolylacetyl, 2- or 3-thienylacetyl, 2- or 3-furylacetyl and 2-amino-4- or 5-thiazolylacetyl or (II) cycloalkyl or cycloalkenyl which may have one to five substituents each selected from a class (B) consisting of alkyl, alkoxy, alkenyl, aryl, aralkyl, mercapto, alkylthio, arylthio, aralkylthio, alkylsulfonyl, arylsulfonyl, aralkylsulfonyl, haloalkyl, hydroxy, oxo, thioxo, halogen, nitro, amino, cyano, carbamoyl, carboxyl, acyl, acyloxy, acylamino, hydroxyalkyl, carboxyalkyl, and mono- or dialkylaminoalkyl, the acyl moiety of acyl and acylamino being as defined above;

$R^3$ is a residue resulting from removal of the α-amino group from an optically active α-amino acid of the formula $R^3NH_2$ and selected from the class consisting of D-aspartic acid, L-aspartic acid, D-asparagine, L-asparagine, D-glutamic acid, L-glutamic acid, D-glutamine, L-glutamine, D-alanine, L-alanine, D-arginine, L-arginine, D-cystathionine, L-cystathionine, D-cystine, L-cystine, D-isoleucine, L-isoleucine, D-lanthionine, L-lanthionine, D-leucine, L-leucine, D-lysine, L-lysine, D-methionine, L-methionine, D-norleucine, L-norleucine, D-norvaline, L-norvaline, D-ornithine, L-ornithine, D-valine, L-valine, or a derivative of such an α-amino acid in which a carboxyl group on $R^3$ is protected (1) by an ester-forming group selected from alkyl*, cycloalkyl*, alkenyl*, alkynyl*, cycloalkenyl*, aryl* and aralkyl*, succinimidomethyl, phenacyl, trityl, 4-mesylbenzoylmethyl, phthalimidomethyl, benzenesulfonylmethyl, and a silyl group of the formula $R^5R^6R^7Si$- wherein $R^5$, $R^6$ and $R^7$ each is a straight or branched $C_{1-6}$ alkyl or a $C_{6-10}$ aryl group or (2) by a group forming an acid amide of such carboxyl group of the formula

wherein Y and W are independently a hydrogen atom, a $C_{1-6}$ alkyl, a $C_{6-11}$ aryl, a $C_{3-8}$ cycloalkyl, or form with the nitrogen atom to which they are attached, pyrrolidino, piperidino, morpholino, N'-methyl-piperazino or

represents 5,6-dihydrophenanthrene amino, or a residue from removal of the α-amino group from another or the same optically active α-amino acid, an amino group, if present, on $R^3$ is unsubstituted or is substituted by alkyl*, cycloalkyl*, aralkyl*, aryl*, heterocyclic* group selected from the class (H) as defined above, amidino, aminomethylene, carbamoyl and sulfoxy group, or protected by an amino-protecting group used in the field of β-lactam and peptide synthesis, and thiol group, if present on $R^3$, is protected by a hydroxyl- or thio-protecting group selected from an acyl group as defined above for $R^2$, arylsulfonyl or aliphatic sulfonyl group, alkyl* silyl group of the formula $R^5R^6R^7Si$ wherein $R^5$, $R^6$ and $R^7$ are as defined above and a pyranyl group; and, in respect to all the above definitions, the alkyl, alkenyl, and alkynyl with a superscript asterisk "*" may have one substituent to three substituents each selected from the class (A) as defined above and the cycloalkyl, cycloalkenyl, aralkyl, aryl, heterocycle and heterocyclic with a superscript asterisk "*" may have one substituent to five substituents each selected from the class (B) as defined above.

2. A compound as claimed in claim 1, namely (3S,4R)-1-[(1S)-(1-methoxycarbonyl-2-methyl)propyl]-3-phthalimido-4-styryl-2-azetidinone.

3. A compound as claimed in claim 1, namely (3S,4R)-1-[(1S)-(1-methoxycarbonyl-2-methyl)propyl-3-benzyloxycarbonylamino-4-styryl-2-azetidinone.

4. A compound as claimed in claim 1, namely (3S,4R)-1-[(1R)-(1-methoxycarbonyl-2-methyl)propyl]-3-phthalimido-4-styryl-2-azetidinone.

5. A compound as claimed in claim 1, namely (3S,4R)-1-[(1R)-(1-methoxycarbonyl-2-methyl)propyl]-3-benzyloxycarbonylamino-4-styryl-2-azetidinone.

6. The compound (3S,4R)-1-[(1S)-(1-methoxycarbonyl-2-phenyl)ethyl]-3-phthalimido-4-styryl-2-azetidinone.

7. The compound (3S,4R)-1-[(1S)-(1-methoxycarbonyl-2-phenyl)ethyl]-3-benzyloxycarbonylamino-4-styryl-2-azetidinone.

8. A compound as claimed in claim 1, namely (3S,4R)-1-[(1R)-(1-carboxy-2-methyl)propyl]-3-phthalimido-4-styryl-2-azetidinone or its dicyclohexylamine salt.

9. A compound as claimed in claim 1, said compound being 1-[(1R)-(1-methoxycarbonyl-2-methyl)-propyl]-3-phthalimido-4-methoxycarbonyl-2-azetidinone.

10. A compound as claimed in claim 1, wherein $R^1$ is phthalimido or benzyloxycarbonylamino.

11. A compound as claimed in claim 1, wherein $R^2$ is styryl group.

12. A compound as claimed in claim 1, wherein the derivative of optically active α-amino acid is a $C_{1-6}$ alkyl* ester, or a $C_{7-13}$ aralkyl* ester of optically actie α-amino acid, the groups with a superscript asterisk "*" having the same meaning as defined in claim 1.

13. A compound as claimed in claim 1, namely (3S,4R)-1-[(1S)-(1-benzyloxycarbonyl-2-methyl)-propyl]-3-phthalimido-4-styryl-2-azetidinone.

14. A compound as claimed in claim 1, namely (3S,4R)-1-[(1S)-[1-[{1-(1S)-methoxycarbonyl-2-methyl)propyl}aminocarbonyl]-2-methyl]propyl]-3-benzyloxycarbonylamino-4-styryl-2-azetidinone.

15. A compound as claimed in claim 1, namely (3S,4R)-1-[(1R)-1,2-di(methoxycarbonyl)ethyl]-3-phthalimido-4-styryl-2-azetidinone.

16. A compound as claimed in claim 1, namely (3S,4R)-1-[(1S)-(1-tert-butoxycarbonyl)ethyl]-3-phthalimido-4-styryl-2-azetidinone.

17. A compound as claimed in claim 1, namely (3S,4R)-1-[(1S)-(1-methoxycarbonyl-3-methylthio)-propyl]-3-phthalimido-4-styryl-2-azetidinone.

18. A compound as claimed in claim 1, namely (3S,4R)-1-[(1S)-(1-methoxycarbonyl-2-carbamoyl)ethyl]-3-phthalimido-4-styryl-2-azetidinone.

19. A compound as claimed in claim 1, namely (3S,4R)-1-[(1S)-{1-(1-pyrrolidine)-carbonyl}ethyl]-3-benzyloxycarbonylamino-4-styryl-2-azetidinone.

20. A compound as claimed in claim 1, namely (3S,4R)-1-[(1S)-1,3-di(methoxycarbonyl)propyl]-3-phthalimido-4-styryl-2-azetidinone.

21. A compound as claimed in claim 1, namely (3S,4R)-1-[(1R)-1,2-di(methoxycarbonyl)ethyl]-3-benzyloxycarbonylamino-4-methoxycarbonyl-2-azetidinone.

* * * * *